US006831090B2

(12) United States Patent
Vite et al.

(10) Patent No.: US 6,831,090 B2
(45) Date of Patent: Dec. 14, 2004

(54) 2,3-OLEFINIC EPOTHILONE DERIVATIVES

(75) Inventors: Gregory D. Vite, Titusville, NJ (US); Robert M. Borzilleri, Lawrenceville, NJ (US); Gerhard Höfle, Braunschweig (DE); Thomas Leibold, Braunschweig (DE)

(73) Assignee: Bristol-Myers Squibb Company, Princeton, NJ (US)

( * ) Notice: Subject to any disclaimer, the term of this patent is extended or adjusted under 35 U.S.C. 154(b) by 168 days.

(21) Appl. No.: 10/242,437

(22) Filed: Sep. 13, 2002

(65) Prior Publication Data

US 2003/0060623 A1 Mar. 27, 2003

Related U.S. Application Data

(62) Division of application No. 09/280,210, filed on Mar. 29, 1999, now Pat. No. 6,498,257.
(60) Provisional application No. 60/082,562, filed on Apr. 21, 1998.

(51) Int. Cl.$^7$ ................................................ A61P 35/00
(52) U.S. Cl. ...................................................... 514/365
(58) Field of Search ......................................... 514/365

(56) References Cited

U.S. PATENT DOCUMENTS

| | | | |
|---|---|---|---|
| 6,194,181 B1 | 2/2001 | Hofmann et al. | 435/18 |
| 6,204,388 B1 | 3/2001 | Danishefsky et al. | 546/340 |
| 6,211,412 B1 | 4/2001 | Georg et al. | 568/309 |

FOREIGN PATENT DOCUMENTS

| | | |
|---|---|---|
| DE | 19701758 | 7/1978 |
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19707505.3 | 9/1998 |
| DE | 19713970 | 10/1998 |
| DE | 879605 | 11/1998 |
| DE | 19720312 | 11/1998 |
| DE | 19821954 | 11/1998 |
| DE | 19726627 | 12/1998 |
| WO | 93/10121 | 5/1993 |
| WO | 97/19086 | 5/1997 |
| WO | 98/08849 | 3/1998 |
| WO | 98/22461 | 5/1998 |
| WO | WO 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/03848 | 1/1999 |
| WO | 99/07692 | 2/1999 |
| WO | WO 99/39694 | 8/1999 |
| WO | WO 99/42602 | 8/1999 |
| WO | WO 99/43320 | 9/1999 |
| WO | WO 99/43653 | 9/1999 |
| WO | WO 99/67252 | 12/1999 |
| WO | WO 00/00485 | 1/2000 |
| WO | WO 00/31247 | 6/2000 |
| WO | WO 00/37473 | 6/2000 |
| WO | WO 00/49021 | 8/2000 |
| WO | WO 00/66589 | 11/2000 |

OTHER PUBLICATIONS

Balog et al., 1996, "Total Synthesis of (−)-Epothilone A", Angew. Chem. Int. Ed. Engl., 35(23–24):2801–2803.
Bertini et al., 1970, "Alkenes from Expoxides by Reductive Elimination with Magnesium Bromide–Magnesium Amalgam", Chem. Commun., 144.
Bollag et al., 1995, "Epothilones, A New Class of Microtubule–stabilizing Agents with a Taxol–like Mechanism of Action", Cancer Res. 55, No. 11, 2325–2333.
Fujisawa et al., 1974, "Deoxygenation of Epoxides to Olefins with FeCl$_3$ n–BuLi System", Chem. Lett., 883–886.
Fujisawa et al., 1978, "Reductive Coupling of Carbonyl Compounds to Olefins by Tungsten Hexachloride–Lithium Aluminum Hydride and Some Tungsten and Molybdenum Carbonyls", J. Org. Chem., 43(12):2477–2479.
Gladysz et al., 1976, "Deoxygenation of Epoxides by Metal Atom Cocondensation", J. Org. Chem., 41(22):3647–3648.
Hofle et al., 1996, "Epothilone A and B—Novel 16–Membered Macrolides with Cytotoxic Activity: Isolation, Crystal Structure, and Conformation in Solution", Angew, Chem. Int. Ed Engl., 35(13/14):1567–1569.
Hofle et al., 1999, "N–Oxidation of Epothilone A–C and O–Acyl Rearrangement to C–19 and C–21—Substituted Epothilones", Angew. Chem. Int. Ed., 38(13/14):1971–1974.

(List continued on next page.)

Primary Examiner—Bruck Kifle
(74) Attorney, Agent, or Firm—Rena Patel; Anastasia P. Winslow

(57) ABSTRACT

The present invention relates to 2,3-position modified epothilone derivatives, methods of preparation of the derivatives, and intermediates therefor. The compounds of the invention as 16-membered macrolides having the general structure,

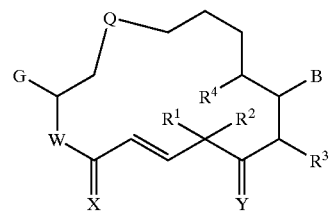

which have microtubule-stabilizing effects and cytotoxic activity against rapidly proliferating cells, such as, tumor cells or other hyperproliferative cellular disease.

36 Claims, No Drawings-

OTHER PUBLICATIONS

Inokuchi et al., 1992, "Opening of Epoxides to Olefins or Halohydrins with Vanadlum(II)–Tetrahydrofuran or Vanadium(III)–Tetrahydrofuran Complexes", Synlett, No. 6, 510–512.

Kowalski et al., 1997, "Activities of the Microtubule–stabilizing Agents Epothilones A and B with Purified Tubulin and in Cells Resistant to Paclitaxel (Taxol®)" J. Biol, Chem., 272(4):2534–2541.

Kupchan et al., 1971, "Reductive Elimination of Epoxides to Olefins with Zinc–Copper Couple", J. Org. Chem., 36(9):1187–1190.

Martin et al., 1984, "Epoxides as Alkene Protecting Groups. A Mild and Efficient Deoxygenation", Tetrahedron Letters, 25(3):251–254.

McMurry et al, 1975, "Reduction of Epoxides to Olefins with Low Valent Titanium", J. Org. Chem., 40(17):2555–2556.

McMurry et al., 1978, "Some Deoxygenation Reaction with Low–Valent Titanium ($TiCl_3$/$LiAlH_4$)", J. Org. Chem., 43(17):3249–3254.

Meng D., et al., "Remote Effects in Macrolide Formation Through Ring–Forming Olefin Metathesis: An Application to the Synthesis of Fully Active Epothilone Congeners", J. Am. Chem. Soc., vol. 119, No. 11, 2733–2734 (1997).

Nicolaou K. C., et al., 1996, "An Approach to Epothilones Based on Olefin Metathesis", Angew. Chem. Int. Ed. Engl., 35(20):2399–2401.

Nicolaou K.C. et al., 1997, "Total Synthesis of Epothilone A: The Macrolactonization Approach", Angew. Chem. Int. Ed. Engl., 36(5): 525–527.

Nicolaou K.C. et al., 1997, Designed Epothilones: Combinatorial Synthesis, Tubulin Assembly Properties, and Cytotoxic Action against Taxoi–Resistant Tumor Cells, Angew. Chem. Int. Ed. Engl., 36(19): 2097–2103.

Nicolaou K.C. et al., 1997, "The Olefin Metathesis Approach to Epothilone A and its Analogues", J. Am. Chem. Soc., 119(34): 7960–7973.

Nicolaou K.C. et al., 1997, "Total Syntheses of Epothilones A and B via a Macrolactonization–Based Strategy", J. Am. Chem. Soc., 119(34): 7974–7991.

Nicolaou K.C. et al., 1997, "Synthesis of Epothilones A and B in Solid and Solution Phase", Nature, 387:268–272.

Nicolaou K.C. et al., 1997, "Synthesis of Epothilones A and B in Solid and Solution Phase" (Correction to Nature 387, 268–272 (1997)), Nature, 390, 100.

Raucher, S., et al., 1986, "Total Synthesis of (+)–Dihydrocostunolide via Tandem Cope–Claisen Rearrangement", J. Org. Chem., 51(26): 5503–5505.

Sato M. et al., 1982, "Reduction of Organic Compounds with Low–Valent Niobium ($NbCl_5$/$NaAlH_4$)", Chem. Letters, 157–160.

Schinzer D. et al., 1997, "Total Synthesis of (–)–Epothilone A", Angew. Chem. Int. Ed. Engl., 36(5):523–524.

Schobert R., et al., 1990, "Reduction and Isomerization of Oxiranes and—Diazoketones by Various Early Transition Metallocenes", Synlett, 8: 465–466.

Sharpless K.B., et al., 1972, "Lower Valent Tungsten Halides. A New Class of Reagents for Deoxygenation of Organic Molecules", J. Amer. Chem. Soc., 94(18):6538–6540.

Su D.–S. et al., 1997, "Total Synthesis of (–)–Epothilone B: An Extension of the Suzuki Coupling Method and Insights into Structure–Activity Realationships of the Epothilones", Angew. Chem. Int. Ed. Engl., 36(7):757–759.

Su D.–S., et al., 1997, "Structure–Activity Relationships of the Epothilones and the First In Vivo Comparison with Paclitaxel", Angew. Chem. Int. Ed. Engl., 36(19):2093–2096.

Victory S.F., et al., 1996, "Relative–Stereochemistry and Solution Conformation of the Novel Pacilitaxel–Like Antimitotic Agent Epothilone A", Bioorg. Med. Chem. Letts., 6(7):893–898.

Winkler J. D. et al., 1996, "A Model For The Taxol (Pacitaxel)/Epothilone Pharmacophore", Bioorg. Med. Chem. Letts., 6(24): 2963–2966.

Yang Z., et al., 1997, "Total Synthesis of Epothilone A: The Olefin Metathesis Approach", Angew. Chem. Int. Ed. Engl., 36(1/2): 166–168.

Bollag D., et al., 1995, "Epothiione, A New Structural Class of Microtubule Stabilizer", Abstract, Proc Am. Assoc. Cancer Res., 36( 86): Meet. 454.

Bollag D., 1997, "Epothilones: Novel Microtubule–Stabilising Agents", Expert Opin. Invest. Drugs, 6(7):867–873.

Bertinato P., et al., 1996, "Studies Toward a Synthesis of Epothilone A; Stereocontrolled Assembly of the Acyl Region and Models for Macrocycilization", J. Org. Chem., 61(23):8000–8001.

Chemical & Engineering News, 1996, "Epothilone Epiphany: Total Syntheses", 74( 52):24–26.

Chemical & Engineering News, 1997, "First Total Synthesis of Epothilone B", 75(13):23.

Chemical & Engineering News, 1997, "Solid–Phase Epothilone Synthesis Used to Create Analog Library", 75( 20):33.

Claus et al., 1997, "Synthesis of the C1–C9 Segment of Epothilons", Tetrahedron Lett., 38(8):1359–1362.

De Brabander et al., 1997 "Towards a Synthesis of Epothilone A: Rapid Assembly of the C1–C6 and C7–C12 Fragments", Synlett, 7: 824–826.

Gabriel T. and Wessjohann, L., 1997, "The Chromium–Reformatsky Reaction; Asymmetric Synthesis of the Aldol Fragment of the Cytotoxic Epothilons from 3–(2–Bromoacyl)–2–Oxazolidinones", Tetrahedron Lett., 38(8):1363–1366.

Gerth K., et al., 1996, "Epothilons A and B: Antifungal and Cytotoxic Compounds from *Sorangiusm celluiosum* (Myxobacteria) Production Physico–chemical and Biological Properties", J. Antibiotics, 49(6):560–563.

Marshall A., "Total Synthesis of Epothilone", Nature Biotechnology, vol. 15, No. 3, 205 (1997).

Meng D., et al., "Studies Toward a Synthesis of Epothilone A: Use of Hydropyran Templates for the Management of Acyclic Stereochemical Relationships", J. Org. Chem., vol. 61, No. 23, 7998–7999 (1996).

Meng D., et al., "Total Syntheses of Epothilones A and B", J. Am. Chem. Soc., vol. 119, No. 42, 10073–10092 (1997).

Mensching, S. and Kalesse, M., "Generation of Thiazoles by Column Dehydrogenation of Thiazolidines with $MnO_2$", J. Prakat. Chem., vol. 339, No. 1, 96–97 (1997).

Mulzer, J. and Mantoulidis, A., "Synthesis of the C(1)–C(9) Segment of the Cytotoxic Macrolides Epothilon A and B", Tetrahedron Lett., vol. 37 No. 51, 9179–9182 (1996).

Nicolaou, K., et al., 1999, "Chemistry, Biology and Medicine of Selected Tubulin Polymerizing Agents", Pur Appl. Chem., 71(6): 989–997.

Nicolaou K., et al., 1997, "Total Synthesis of Epothilone E and Related Side –chain Modified Analogues Via a Stille Coupling Based Strategy", Bioorg. Med. Chem., 7(5): 665–697.

Schinzer D., et al., 1996, "Studies Towards the Synthesis of Epothilones: Asymmetric Synthesis of the Key Fragments", Chem. Eur. J., 2(22): 1477–1482.

Taylor and Haley, J., 1997, "Towards the Synthesis of Epothilone A: Enantioselective Preparation of the Thiazole Sidechain and Macrocyclic Ring Closure", Tetrahedron Lett., 38(12):2061–2064.

Schinzer D., et al., 1999, "Synthesis of (–)-Epothilone B", Chem. Eur. J., 5(9):2492–2500.

Schinzer D., et al., 1999, "Syntheses of (–)-Epothilone B", Chem. Eur. J., 5(9): 2492–2500.

Nnicolaou K. C., et al., 1998, "Synthesis and Biological Properties of C12, 13–Cyclopropylepothilone A and Related Epothilones", Chemistry & Biology, 5(7): 365–372.

Altmann et al., 2000, "Epothilones and Related Structures—A New Class of Microtubule Inhibitors with Potent in Vivo Antitumor Activity," Biochem. Biophys. Acta, 1470:M79–M91.

Nicolaou et al., 1998, "Total Synthesis of Epothilone E and Analogs with Modified Side Chains Through the Stille Coupling Reaction," Angew. Chem. Int. Ed. 37:84–87.

Nicolaou et al., 1998, "Chemistry and Biology of Epothilones," Angew. Chem. Int. Ed. 37:2014–2045.

2,3-OLEFINIC EPOTHILONE DERIVATIVES

CROSS-REFERENCE TO RELATED APPLICATIONS

This is a divisional of U.S. application Ser. No. 09/280,210, filed Mar. 29, 1999, now U.S. Pat. No. 6,498,257, which claims the benefit of priority of U.S. Provisional Application No. 60/082,562 filed Apr. 21, 1998, which is incorporated herein by reference in its entirety.

FIELD OF THE INVENTION

The present invention relates to epothilone derivatives, methods for the preparation of the derivatives and intermediates therefor.

BACKGROUND OF THE INVENTION

Epothilones are macrolide compounds which find utility in the pharmaceutical field. For example, Epothilones A and B having the structures:

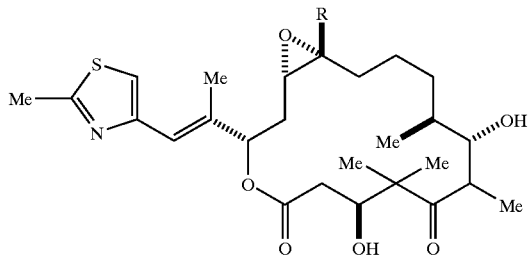

Epothilone A R=H
Epothilone B R=Me have been found to exert microtubule-stabilizing effects similar to TAXOL and hence cytotoxic activity against rapidly proliferating cells, such as, tumor cells or other hyperproliferative cellular disease, see *Angew. Chem. Int. Ed. Engl.*, 1996, 35, No. 13/14.

SUMMARY OF THE INVENTION

The present invention relates to compounds of the formula

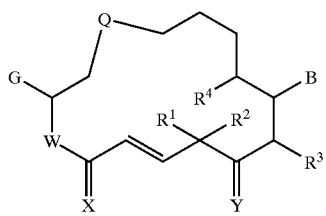

Q is selected from the group consisting of

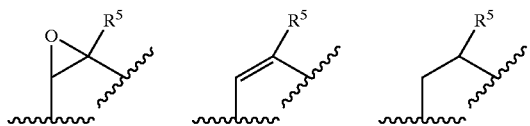

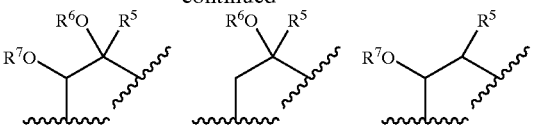

G is selected from the group consisting of alkyl, substituted alkyl, aryl, substituted aryl, heterocyclo,

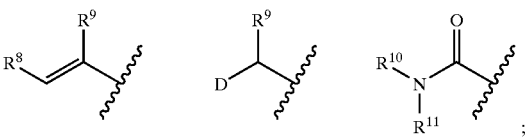

W is O or N $R_{12}$;
X is O, S, or H, H;
Y is selected from the group consisting of O; H, $OR_{13}$; $OR_{14}$, $OR_{14}$; $NOR_{15}$; H, $NOR_{16}$; H, $NR_{17}R_{18}$; H, H; or $CHR_{19}$; $OR_{14}$ $OR_{14}$ can be a cyclic ketal;
B is selected from the group consisting of H, $OR_{20}$, or $OCOR_{21}$, and $NR_{22}R_{23}$;
D is selected from the group consisting of $NR_{24}R_{25}$ or saturated heterocycle (such as piperidinyl, pyrrolidinyl, and the like);
$R_1$, $R_2$, $R_3$, and $R_4$ are selected from H or lower alkyl;
$R_{15}$, $R_{16}$, $R_{17}$, $R_{18}$, and $R_{19}$ are selected from the group H, alkyl, substituted alkyl, or aryl;
$R_6$, $R_7$, $R_{13}$, $R_{14}$, $R_{20}$, and $R_{21}$ are selected from the group H, alkyl, or substituted alkyl;
$R_5$, $R_8$, $R_9$, $R_{22}$, $R_{24}$, $R_{26}$, and $R_{27}$ are selected from the group consisting of H, alkyl, substituted alkyl, aryl, heteroaryl, cycloalkyl, or heterocyclo;
$R_{12}$, $R_{23}$, and $R_{25}$ are selected from the group consisting of H, alkyl, substituted alkyl, aryl, heteroaryl, cycloalkyl, heterocyclo, $R_{26}C=O$, $R_{27}SO_2$, hydroxy, O-alkyl or O-substituted alkyl;
and any salts, solvates or hydrates thereof
Proviso
The present invention does not include compounds of formula I wherein
W and X are both O; and
$R_1$, $R_2$, $R_3$, $R_4$ are methyl; and
$R_5$ is H or methyl; and
G is 1-methyl-2-(2-methyl-4-thiazolyl)ethenyl; and
Q is

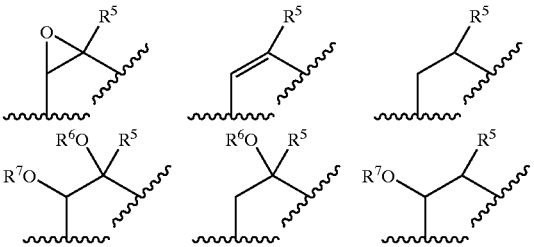

DETAILED DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, phenyl, substituted phenyl, heterocyclo, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

The term "heteroatoms" shall include oxygen, sulfur and nitrogen.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be obtained, for example, by exchanging the carboxylic acid protons, if they contain a carboxylic acid, in compounds of formula I with the desired ion in a medium in which the salt precipitates or in an aqueous medium followed by evaporation. Other salts can be formed as known to those skilled in the art.

The compounds for formula I form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts are formed by reacting a compound of formula V in an equivalent amount of the acid in a medium in which the salt precipitates or in an aqueous medium followed by evaporation.

In addition, zwitterions ("inner salts") are formed.

Compounds of the formula I may also have prodrug forms. Any compound that will be converted in vivo to provide the bioactive agent (i.e., the compound for formula I) is a prodrug within the scope and spirit of the invention.

For example compounds of the formula I may form a carboxylate ester moiety. The carboxylate esters are conveniently formed by esterifying any of the carboxylic acid functionalities found on the disclosed ring structure(s).

Various forms of prodrugs are well known in the art. For examples of such prodrug derivatives, see:

a) *Design of Prodrugs,* edited by H. Bundgaard, (Elsevier, 1985) and *Methods in Enzymology,* Vol.42, p. 309–396, edited by K. Widder, et al. (Acamedic Press, 1985);
b) *A Textbook of Drug Design and Development,* edited by Krosgaard-Larsen and H. Bundgaard, Chapter 5, "Design and Application of Prodrugs," by H. Bundgaard, p. 113–191 (1991);
c) H. Bundgaard, *Advanced Drug Delivery Reviews,* 8, 1–38 (1992);
d) H. Bundgaard, et al., *Journal of Pharmaceutical Sciences,* 77, 285 (1988); and
e) N. Kakeya, et al., *Chem Phar Bull,* 32, 692 (1984).

It should further be understood that solvates (e.g., hydrates) of the compounds of formula I are also within the scope of the present invention. Methods of solvation are generally known in the art.

Use and Utility

The compounds of formula I are microtubule-stabilizing agents. They are thus useful in the treatment of a variety of cancers or other abnormal proliferative diseases, including (but not limited to) the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, and rhabdomyoscaroma, and osteosarcoma; and other tumors, including melanoma, xenoderma pigmentosum, keratoactanthoma, seminoma, thyroid follicular cancer and teratocarcinoma.

Compounds of formula I may also inhibit tumor angiogenesis, thereby affecting abnormal cellular proliferation. Such anti-angiogenesis properties of the compounds of formula I may also be useful in the treatment of certain forms of blindness related to retinal vascularization, arthritis, especially inflammatory arthritis, multiple sclerosis, restinosis and psoriasis.

Compounds of formula I may induce or inhibit apoptosis, a physiological cell death process critical for normal development and homeostasis. Alterations of apoptotic pathways contribute to the pathogenesis of a variety of human diseases. Compounds of formula I, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

The compounds of this invention are also useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I can be used sequentially with known anticancer or cytotoxic agents and treatment, including radiation when a combination formulation is inappropriate. Especially useful are cytotoxic drug combinations wherein the second drug chosen acts in a different phase of the cell cycle, e.g. S phase, than the present compounds of formula I which exert their effects at the $G_2$-M phase.

The present compounds may exist as multiple optical, geometric, and stereoisomers. Included within the present invention are all such isomers and mixtures thereof.

The compounds of this invention can be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds are administered in a dosage range of about 0.05 to 200 mg/kg/day, preferably less than 100 mg/kg/day, in a single dose or in 2 to 4 divided doses.

Method of Preparation

A compound of formula I can be prepared as shown in Scheme 1, using procedures described in PCT/EP96/05080. A compound of formula 1.A can be esterified using, for example, a mixture of formic acid and acetic anhydride to give a corresponding diformate 1.B. A compound of formula 1.C can be prepared from a compound of formula 1.B using a base such as DBU. A compound of formula I can be prepared from a compound of formula 1.C by treatment with methanolic ammonia.

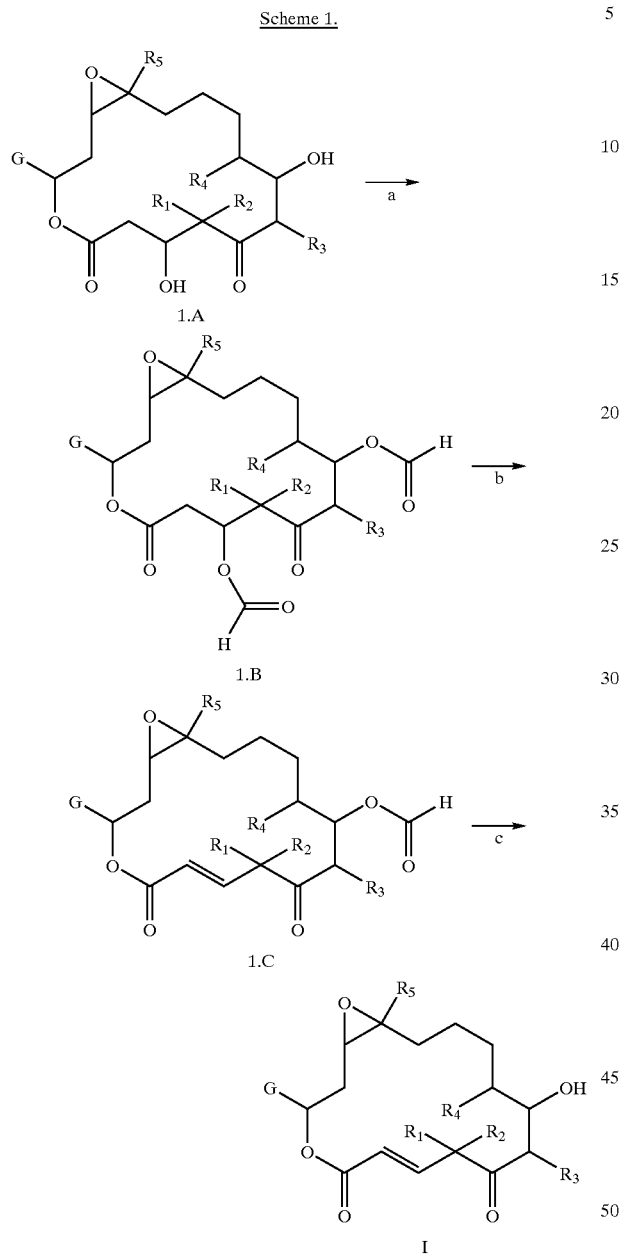

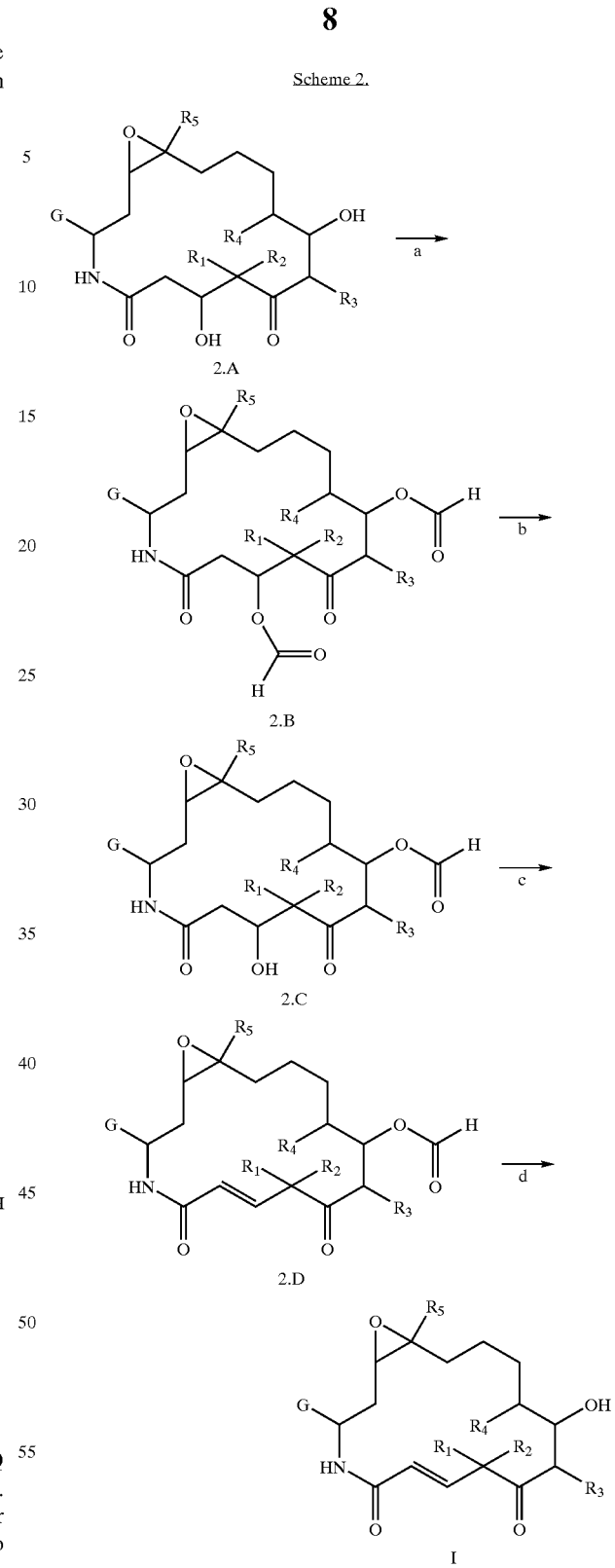

Compounds of formula I where X is O, W is NH, and Q is an oxiranyl group can be prepared as shown in Scheme 2. A compound of formula 2.A can be esterified using, for example, a mixture of formic acid and acetic anhydride to give a corresponding diformate 2.B. A compound of formula 2.C can be prepared from a compound of formula 2.B by treatment with a base such as DBU. A compound of formula 2.D can be prepared from a compound of formula 2.C using for example methanesulfonyl chloride and triethylamine, or Burgess' reagent. Treatment of a compound of formula 2.D with methanolic ammonia affords a compound of formula I where X is NH and Q is an oxiranyl group.

A compound of formula 2.A where G is —$CR_9$=$CR_8H$ can be prepared as shown in Scheme 3. A compound of formula 3.B can be prepared from a compound of formula 3.A (an epothilone or epothilone-related natural product) by formation of pi-allylpalladium complex using, for example, palladium tetrakistriphenylphosphine followed by treatment with sodium azide (see, for example: Murahashi, S.-I.; et.

al., J. Org. Chem. 1989, 54, 3292). Subsequent reduction of a compound of formula 3.B with a reducing agent such as triphenylphosphine provides a compound of formula 3.C. A compound of formula 3.D (or 2.A where G is —CR$_9$=CR$_8$H) can be prepared from a compound of formula 3.C by macrolactamization using, for example, diphenylphosphoryl azide (DPPA) or bromotripyrrolidinophosphonium hexafluorophosphate (PyBroP).

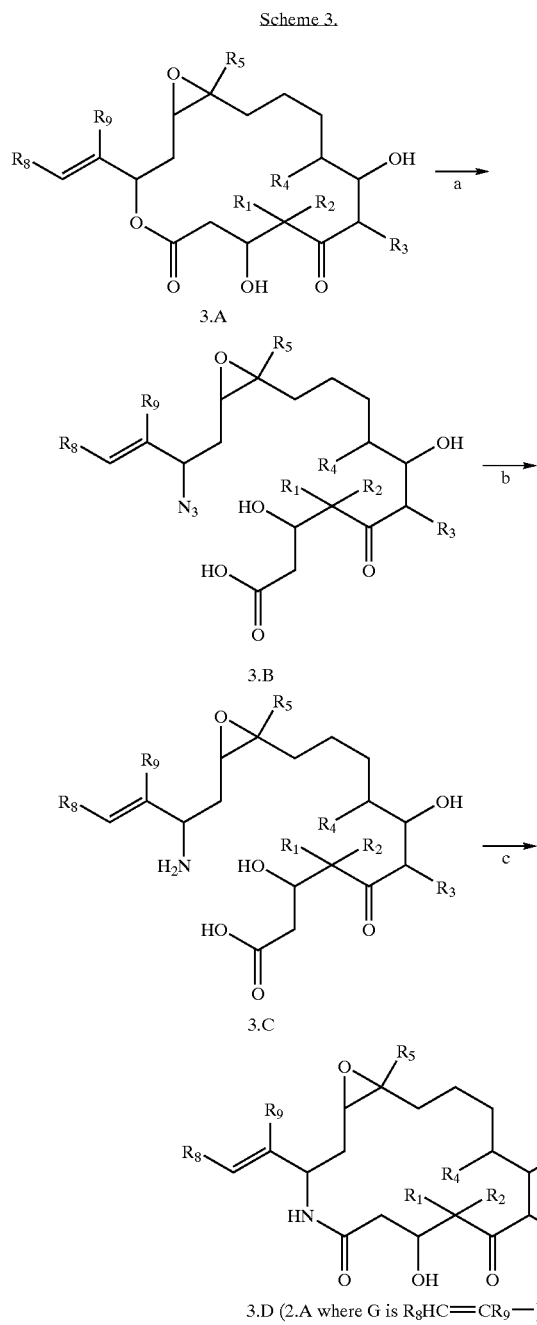

A compound of formula I where W is O and X is H,H can be prepared as shown in Scheme 4. The alcohol moiety of a compound of formula I where both W and X are O can be protected using methods in the art to give a compound of formula 4.A, where P$_1$ is a suitable O-protecting group such as triethylsilyl. Hydrolysis of a compound of formula 4.A, using for example lithium hydroxide monohydrate, provides a compound of formula 4.B. Esterification of a compound of formula 4.B, using for example trimethylsilyl diazomethane, provides a compound of formula 4.C. Selective dihydroxylation of the α,β-unsaturated ester moiety of a compound of formula 4.C by known methods (see Sharpless, K. B. et al., J. Org. Chem. (1992) 57, 2768) provides a compound of formula 4.D. Oxidative cleavage of the diol of a compound of formula 4.D, using for example lead tetraacetate provides a compound of formula 4.E. A compound of formula 4.F can be prepared from a compound of formula 4.E using an allylating agent such as ally bromide and a silver salt such as silver oxide. A compound of formula 4.G can be prepared from a compound of formula 4.F using an olefinating agent such as methyltriphenylphosphonium bromide and a base such as sodium hexamethyldisilazide. A compound of formula 4.H can be prepared from a compound of formula 4.G by ring-closing metathesis using either the Grubbs (RuCl$_2$(=CHPh)(PCY$_3$)$_2$; see Grubbs, R. H., et al., Angew. Chem. Int. Ed. Engl.; (1995) 34, 2039) or Schrock catalysts (see Schrock, R. R., et al., J. Am. Chem. Soc., (1990) 112, 3875). A compound of formula I where W is O and X is H,H can be prepared from a compound of formula 4.H by removal of the protecting group using for example acetic acid/THF/water mixtures.

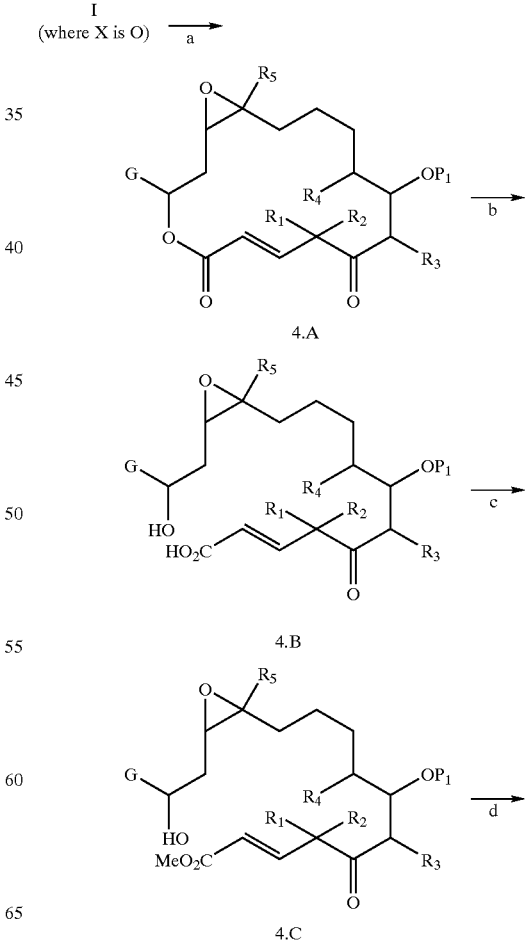

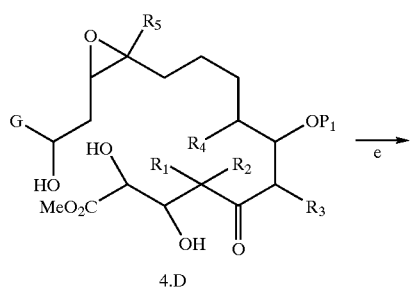

4.D

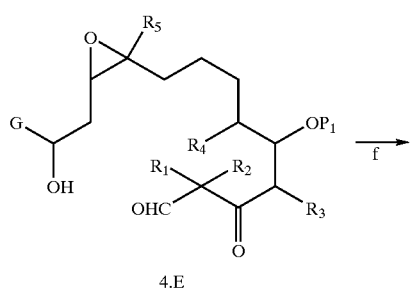

4.E

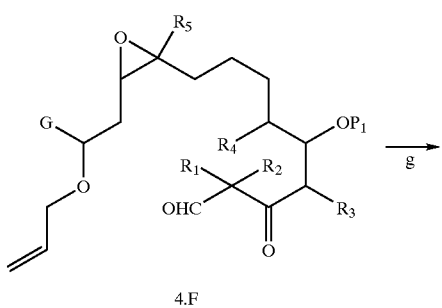

4.F

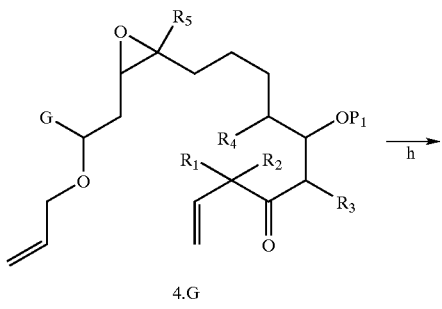

4.G

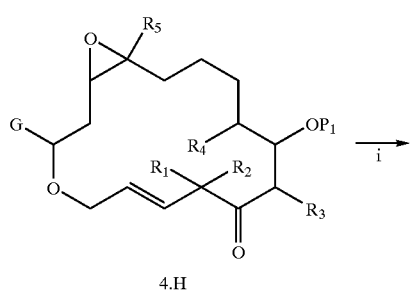

4.H

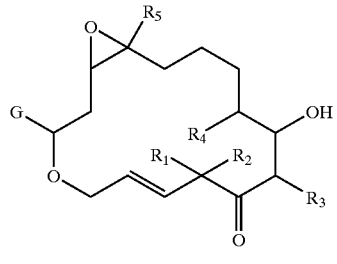

I (where X is H, H)

Alternatively, compounds of formula I where X is H,H can be prepared as shown is Scheme 5. A compound of formula I where X is S can be prepared from a compound of formula I where X is O using, for example, Lawesson's reagent [2,4-bis(4-methoxyphenyl)-1,3-dithia-2,4-diphosphetane-2,4-disulfide]. A compound of formula I where X is H,H can be prepared from a compound of formula I where X is S by reduction with reducing agents such as tri-n-butyltin hydride, Raney nickel, or nickel boride. In Scheme 5, the hydroxyl group can be optionally protected using, for example, a triethylsily group which can be removed ultimately by treatment with hydrogen fluoride-pyridine or acetic acid/THF/water mixtures.

Scheme 5.

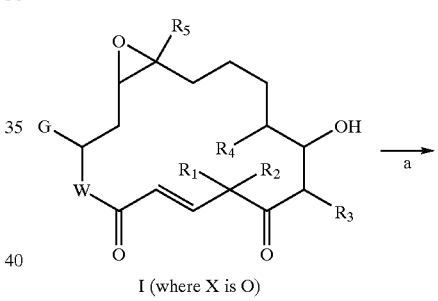

I (where X is O)

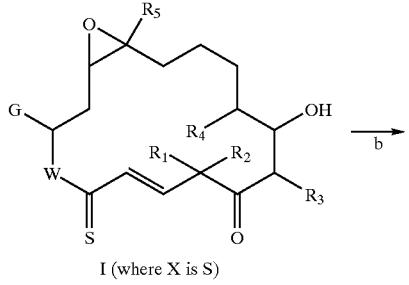

I (where X is S)

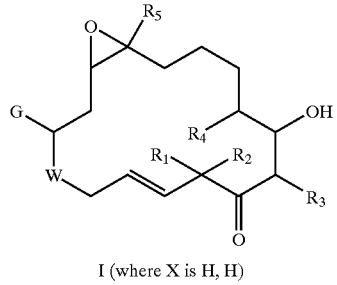

I (where X is H, H)

Compounds of formula I where Q is an olefinic group or the corresponding saturated derivative can be prepared as shown in Scheme 6. Compounds of formula I where Q is an oxiranyl group (i.e., compound 6.A) can be reduced using reagents such as reactive titanocene or tungsten chloride and butyllithium to provide compounds of formula I where Q is an olefinic group (i.e., compound 6.B). Further reduction using, for example, diimide provides compounds of formula I where Q is a saturated alkyl chain (i.e., compound 6.C).

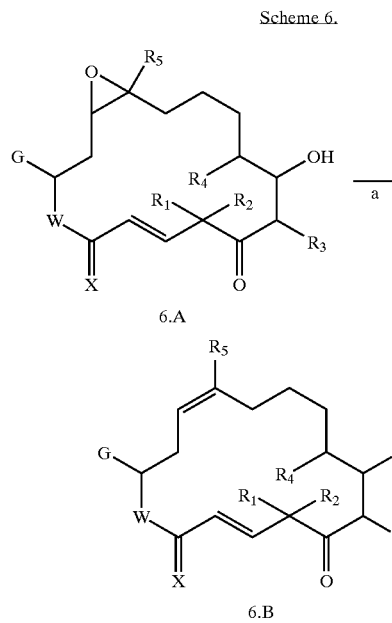

In Schemes 1, 3, 4, and 5, the starting material can be obtained from fermentation of Sorangium cellulosum as previously described (see Angew. Chem. Int. Ed. Engl., 1996, 35, No. 13/14.). In these fermentation products G is usually, but not exclusively, selected from the following:

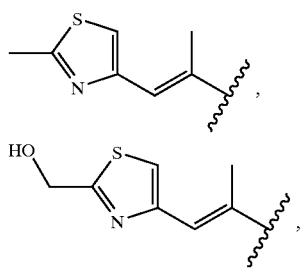

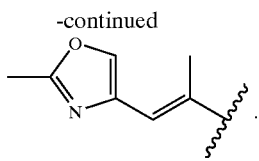

In cases where G is not selected from the preceding list or obtained from fermentation, synthetic methods can be used. For example, total synthesis routes have been described (See, for example: Danishefsky, S. J., et. al., *J. Am. Chem. Soc.,* (1997) 119, 10073), and these methods can be used to provide compounds of formula IA where G is, for example, alkyl, substituted alkyl, aryl, substituted aryl, heterocyclo, and —$CR_9$=$CR_8H$. In addition, semi-synthesis which utilizes degradation of natural epothilones can be employed. For example, epothilones (i.e., 7.A) can be protected and then degraded to a compound of formula 7.B (see PCT/EP96/05080). Subsequent, olefination and deprotection provides compounds of formula 1.A where is —$CCH_3$=$CR_8H$ (i.e., compound 7.C). Alternatively, 7.B can be treated with an alkyl or arylmagnesium halide to provide a tertiary alcohol which can be dehydrated using, for example, Burgess reagent to provide a compound of formula 1.A where is —$CCH_3$=$CR_8H$ (i.e., compound 7.C).

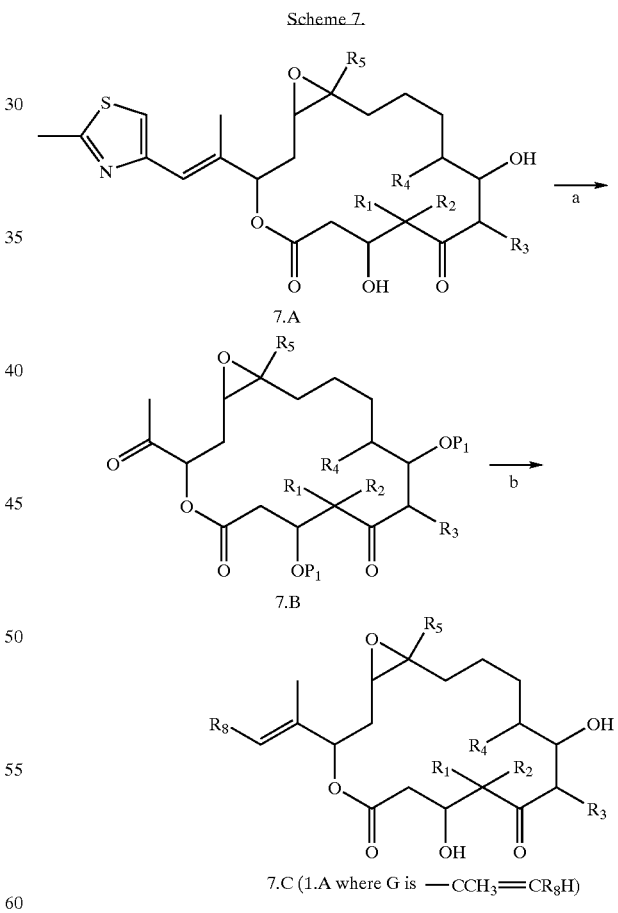

Furthermore, starting compounds of formula 1.A where G is —$C(O)NR_{10}R_{11}$ can be prepared from a compound of formula 7.B as shown in Scheme 8. A compound of formula 8.A where P is a trialkylsilyl group can be prepared from a compound of formula 7.B using for example t-butyldimethylsilyl chloride and triethylamine. Oxidative cleavage of a compound of formula 8.A using for example ozone provides a compound of formula 8.B. Amide coupling of a compound of formula 8.B using methods well known in the art followed by deprotection provides a compound of 1.A where G is —C(O)NR$_{10}$R$_{11}$ (i.e., compound 8.C).

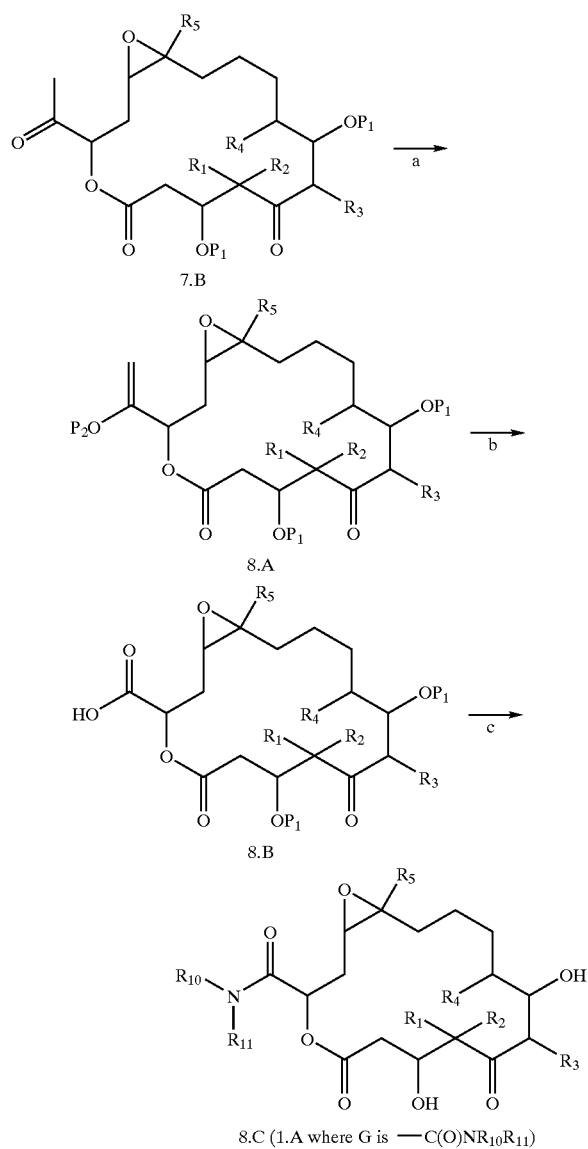

The in vitro assessment of biological activity of the compounds of formula I was performed as follows:

In vitro Tubulin Polymerization. Twice cycled (2×) calf brain tubulin was prepared following the procedure of Williams and Lee (see Williams, R. C., Jr., and Lee, J. C. Preparation of tubulin from brain. Methods in Enzymology 85, Pt. D: 376–385, 1982) and stored in liquid nitrogen before use. Quantification of tubulin polymerization potency is accomplished following a modified procedure of Swindell, et al., (see Swindell, C. S., Krauss, N. E., Horwitz, S. B., and Ringel, I. Biologically active taxol analogues with deleted A-ring side chain substituents and variable C-2' configurations. J. Med. Chem. 34: 1176–1184, 1991). These modifications, in part, result in the expression of tubulin polymerization potency as an effective concentration for any given compound. For this method, different concentrations of compound in polymerization buffer (0.1M MES, 1 mM EGTA, 0.5 mM MgCl$_2$, pH 6.6) are added to tubulin in polymerization buffer at 37° in microcuvette wells of a Beckman (Beckman Instruments) Model DU 7400 UV spectrophotometer. A final microtubule protein concentration of 1.0 mg/ml and compound concentration of generally 2.5, 5.0, and 10 μM are used. Initial slopes of OD change measured every 10 seconds were calculated by the program accompanying the instrument after initial and final times of the linear region encompussing at least 3 time points were manually defined. Under these conditions linear variances were generally <10$^{-6}$, slopes ranged from 0.03 to 0.002 absorbance unit/minute, and maximum absorbance was 0.15 absorbance units. Effective concentration (EC$_{0.01}$) is defined as the interpolated concentration capable of inducing an initial slope of 0.01 OD/minute rate and is calculated using the formula: EC$_{0.01}$=concentration/slope. EC$_{0.01}$ values are expressed as the mean with standard deviation obtained from 3 different concentrations. EC$_{0.01}$ values for the compounds in this invention fall in the range 0.01–1000 μM.

Cytoxicity (In-Vitro)

Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et. al., "Comparison of MTT, XTT, and a novel tetrazolium compound MTS for in vitro proliferation and chemosensitivity assays.," Mol. Biol. Cell 3 (Suppl.):184a, 1992. Cells were plated at 4,000 cell/well in 96 well microtiter plates and 24 hours later drugs were added and serial diluted. The cells were incubated at 37° form 72 hours at which time the tetrazolium dye, MTS at 333 μg/ml (final concentration), in combination with the electron coupling agent phenazine methosulfate at 25 μM (final concentration) was added. A dehydrogenase enzyme in live cells reduces the MTS to a form that absorbs light at 492 nM which can be quantitated spectrophotometrically. The greater the absorbance the greater the number of live cells. The results are expressed as an IC$_{50}$, which is the drug concentration required to inhibit cell proliferation (i.e. absorbance at 450 nM) to 50% of that of untreated control cells. The IC$_{50}$ values for compounds of this invention fall in the range 0.01–1000 nM.

Preferred Compounds

As preferred compounds of the present invention are compounds of formula I wherein Q is selected from the group consisting of

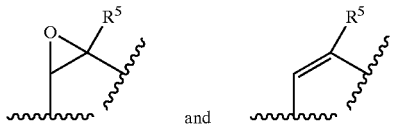

and y is oxygen.

EXAMPLE 1

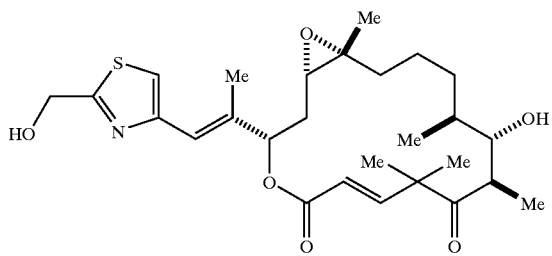

[1S-[1R*,3R*(E),7R*,10S*,11R*,12R*,16S*]]-11-Hydroxy-8,8,10,12,16-pentamethyl-3-[1-methyl-2-(2-hydroxymethyl4-thiazolyl)ethenyl]-4,17-dioxabicyclo[14.1.0]heptadec-6(E)-ene-5,9-dione.

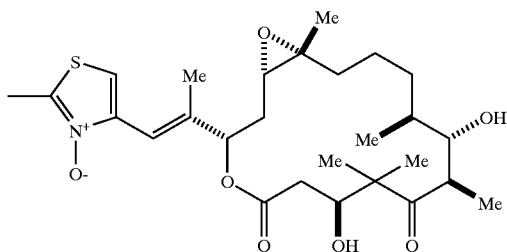

A. [1S-[1R*,3R*(E),7R*,10R*,11S*,12R*,16S*1]]-7,11-Dihydroxy-8,8,10,12,16-pentamethyl-3-[1-methyl-2-(2-methyl-4-thiazolyl)ethenyl]-4,17-dioxabicyclo[14.1.0]heptadecane-5,9-dione, N-oxide.

A solution of epothilone B (2.0 g, 3.9 mmol) in CH$_2$Cl$_2$ (30 mL) was treated with 3-chloroperoxybenzoic acid (1.0 g, 5.9 mmol) at 25° C., under Ar for 2 h. An additional 0.5 g (3.0 mmol) of 3-chloroperoxybenzoic acid was added and the reaction mixture was then stirred for 2 h. The reaction mixture was filtered and the filtrate was concentrated in vacuo. The residue was dissolved in EtOAc (100 mL), washed with saturated aqueous NaHCO$_3$ (75 mL), 5 % aqueous Na$_2$SO$_3$ (75 mL), H$_2$O (75 mL), dried (Na$_2$SO$_4$) and concentrated in vacuo. The residue was purified by flash chromatography (SiO$_2$, 4.5×30 cm, 2–10% MeOH—CHCl$_3$ gradient elution) to afford Compound A (1.04 g, 50%) as a white solid. MS (ESI$^+$): 524.3 (M+H)$^+$; MS (ESI$^-$): 522.5 (M–H)$^-$.

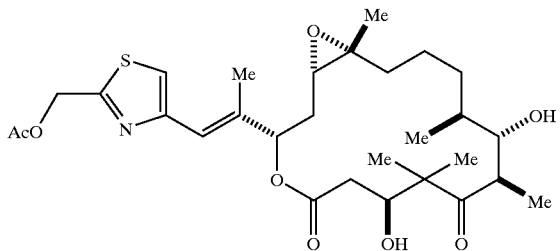

B. [1S-[1R*,3R*(E),7R*,10S*,11R*,12R*,16S*]]-7,11-Dihydroxy-8,8,10,12,16-pentamethyl-3-[1-methyl-2-(2-acetoxymethyl4-thiazolyl)ethenyl]-4,17-dioxabicyclo[14.1.0]heptadecane-5,9-dione. To a resealable Kontes vial was added compound A (0.20 g, 0.38 mmol) and acetic anhydride (2 mL) under Ar. The reaction vessel was sealed under Ar and heated to 75° C. for 4 min. Acetic acid (0.4 mL) was then introduced into the reaction vessel and the reaction mixture was heated for an additional 30 min at 75° C. After the Kontes vial was cooled to 25° C., the volatiles were removed it vacuo and the residue was purified by flash chromatography (SiO$_2$, 3.0×15 cm, 45:45:10 hexane/tert-butyl methyl ether/MeOH) to afford Compound B (0.15 g, 68%) as a colorless oil. MS (ESI$^+$): 566.2 (M+H)$^+$, 1131.5 (2M+H)$^+$; MS (ESI$^-$): 564.4 (M–H)$^-$, 1129.7 (2M–H)$^-$.

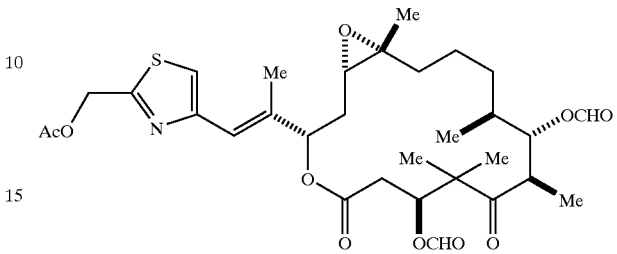

C. [1S-[1R*,3R*(E),7R*,10S*,11R*,12R*,16S*]]-7,11-Dihydroxy-8,8,10,12,16-pentamethyl-3-[1-methyl-2-(2-acetoxymethyl-4-thiazolyl)ethenyl]-4,17-dioxabicyclo[14.1.0]heptadecane-5,9-dione, 7,11 diformate.

A solution of compound B (0.15 g, 0.27 mmol) in CH$_2$Cl$_2$ (5 mL) was treated with 4-N,N-dimethylaminopyridine (71 mg, 58 mmol), triethylamine (0.37 mL, 2.6 mmol), and formic acid (50 mL, 1.3 mmol) at 25° C., under Ar. The reaction mixture was cooled to –15° C. and acetic anhydride (0.12 mL, 1.3 mmol) was added over 3 min. The reaction mixture was stirred at –15° C. (15 min), warmed to 25° C. (15 min), quenched with pH 7.0 phosphate buffer and extracted with EtOAc (3×30 mL). The combined organic extracts were washed with aqueous 1 N HCl (50 mL), 10% aqueous NaHCO$_3$ solution (50 mL), brine (50 mL), dried (Na$_2$SO$_4$), and concentrated in vacuo. The residue was purified by flash chromatography (SiO$_2$, 1.5×10 cm, 10% acetone-CH$_2$Cl$_2$) to afford Compound C (0.134 g, 84%) as a glass. MS (ESI$^+$): 622.2 (M+H)$^+$.

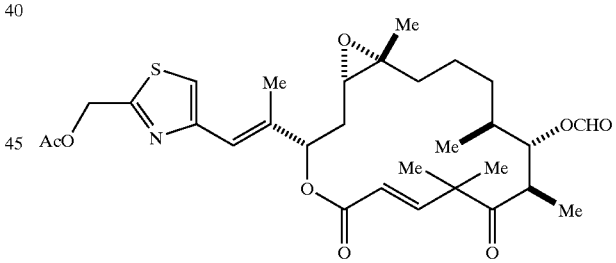

D. [1S-[1R*,3R*(E),7R*,10S*,11R*,12R*,16S*]]-11-Hydroxy-8,8,10,12,16-pentamethyl-3-[1-methyl-2-(2-acetoxymethyl-4-thiazolyl)ethenyl]-4,17-dioxabicyclo[14.1.0]heptadee-6(E)-ene-5,9-dione, 11-formate.

A solution of compound C (0.13 g, 0.21 mmol) in CH$_2$Cl$_2$ (2.2 mL) was treated with 1,8-diazabicyclo[5.4.0]undec-7-ene (0.31 mL, 2.1 mmol) at 25° C., under Ar. The reaction mixture was stirred at 25° C., for 2 h, quenched by the addition of pH 4.0 phosphate buffer, and extracted with EtOAc (3×20 mL). The combined organic extracts were washed with saturated aqueous NaHCO$_3$ solution (30 mL), brine (30 mL), dried (Na$_2$SO$_4$), and concentrated in vacuo. The residue was purified by flash chromatography (SiO$_2$, 1.5×10 cm, 25–50% EtOAc-hexane gradient elution) to afford Compound D (0.11 g, 92%) as a foam. MS (ESI$^+$): 576.2 (M+H)$^+$.

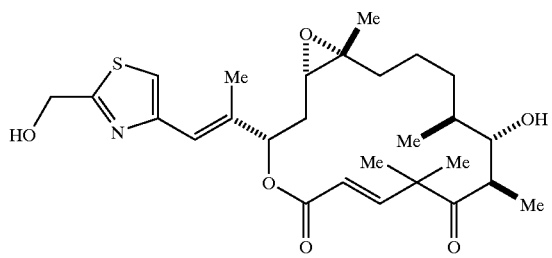

E. [1S-[1R*,3R*(E),7R*,10S*,11R*,12R*,16S*]]-11-Hydroxy-8,8,10,12,16-pentamethyl-3-[1-methyl-2-(2-hydroxymethyl-4-thiazolyl)ethenyl]-4,17-dioxabicyclo[14.1.0]heptadec-6(E)-ene-5,9-dione.

A solution of compound D (0.11 g, 0.19 mmol) in MeOH (1.0 mL) was treated with 2 M ammonia in methanol (1.0 mL) at 25° C., under Ar. The reaction mixture was warmed to 45° C. for 1 h and concentrated in vacuo. The residue was purified by flash chromatography (SiO$_2$, 1.5×10 cm, 2–5% MeOH—CHCl$_3$ gradient elution) to afford the title compound (95 mg, 98%) as a white foam. MS (ESI$^+$): 506.2 (M+H)$^+$, 1011.3 (2M+H)$^+$; MS (ESI$^-$): 504.5 (M–H)$^-$.

EXAMPLE 2

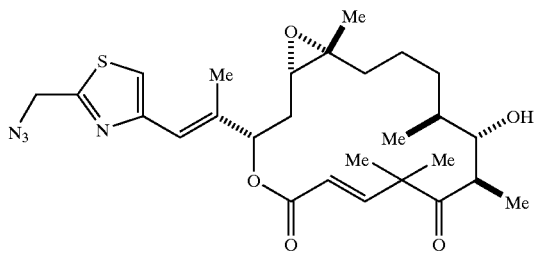

[1S-[1R*,3R*(E),7R*,10S*,11R*,12R*,16S*]]-11-Hydroxy-8,8,10,12,16-pentamethyl-3-[1-methyl-2-(2-azidomethyl-4-thiazolyl)ethenyl]-4,17-dioxabicyclo[14.1.0]heptadec-6(E)-ene-5,9-dione.

To a stirred solution of Compound 1E (3.0 mg, 0.0059 mmol) in 0.5 mL THF at 0C. was added a 0.2M solution of diphenylphosphoryl azide (DPPA) in THF (35 μl, 0.0071 mmol, 1.2 eq) followed by addition of a 0.2M solution of DBU in THF (30 μL, 0.0060 mmol, 1 eq). The mixture was allowed to stir at 0C. for 3.5 h. An additional 15 μL of DPPA solution (0.0030 mmol, 0.5 eq) and 30 μL of DBU solution (0.0060 mmole, 1 eq) were added, and the mixture was allowed to stir at 0C. for an additional 20 min. The solution was then warmed to 25C. and allowed to stir for 15 h. The mixture was diluted with 60 mL ethyl acetate then washed with 10 mL water and dried over Na$_2$SO$_4$. The organic layer was concentrated in vacuo and purified by silica gel chromatography using 2.5% MeOH in CHCl3 to afford 2 mg of a clear film (65%). M+H=531.2.

What is claimed:

1. A method of treating breast cancer, ovarian cancer, colon cancer, head a d neck cancer, lung cancer, cervical cancer, uterine cancer, rain cancer, germ cell cancer, urothelial cancer, esophageal cancer, prostrate cancer , bladder cancer, or pancreatic cancer in a patient in need of said treatment which comprises administering to said patient a therapeutically effective amount of a compound of formula:

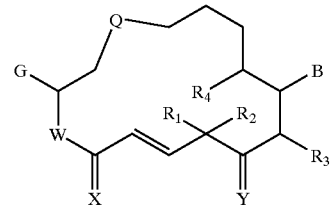

(I)

wherein:

Q is selected from the group consisting of:

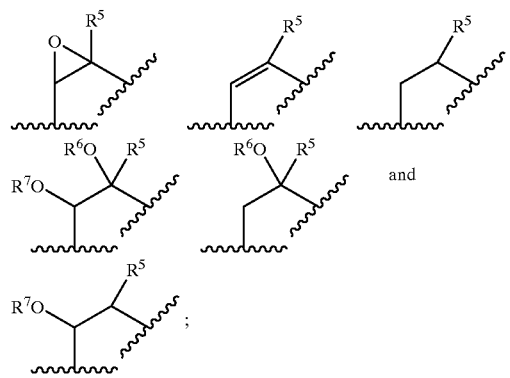

G is selected from the group consisting of: alkyl, substituted alkyl, aryl, substituted aryl, heterocyclo,

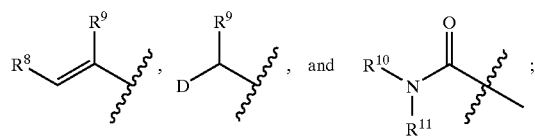

W is O;

X is O; S; or H, H;

Y is selected from the group consisting of: O; NOR$_{15}$; CHR$_{19}$; H and H; H and OR$_{13}$; OR$_{14}$ an OR$_{14}$; H and NR$_{17}$R$_{18}$; and H and NHOR$_{16}$, wherein when Y is OR$_{14}$, OR$_{14}$ the R$_{14}$ groups can be joined to form a cyclic ketal;

B is selected from the group consisting of: H, OR$_{20}$, OCOR$_{21}$, and NR$_{22}$R$_{23}$;

D is NR$_{24}$R$_{25}$ or saturated heterocyclo;

each R$_1$, R$_2$, R$_3$, and R$_4$ is, independently, H or lower alkyl;

each R$_{15}$, R$_{16}$, R$_{17}$, R$_{18}$, and R$_{19}$ is, independently, selected from the group consisting of: H alkyl, substituted alkyl, and aryl; each R$_6$, R$_7$, R$_{13}$, R$_{14}$, R$_{20}$ and R$_{21}$ is, independently, selected from the group consisting of: H alkyl and substituted alkyl;

each R$_5$, R$_9$, R$_{10}$, R$_{11}$, R$_{22}$, R$_{24}$, R$_{26}$ and R$_{27}$ is, independently, selected from the group consisting of: H, alkyl, substituted alkyl, aryl, heteroaryl, cycloalkyl and heterocyclo;

R$_8$ is selected from the group consisting of H, alkyl, substituted alkyl, cycloalkyl, and heterocyclo;

each R$_{23}$ and R$_{25}$ is, independently, selected from the group consisting of: H, alkyl, substitute alkyl, aryl, heteroaryl, cycloalkyl, heterocyclo, R$_{26}$C=O, R$_{27}$SO$_2$, hydroxy, O-alky and O-substituted alkyl;

or pharmceutically acceptable salts, hydrates, solvates, or stereoisomers thereof, with the proviso that compounds of the Formula (I) do not include compounds wherein each of:

X is O;

$R_1$, $R_2$, $R_3$, $R_4$ are methyl;

$R_5$ is H or methyl; and

G is 1-methyl-2-(2-methyl-4-thiazolyl)ethenyl.

2. The method of claim 1, wherein the cancer is cancer of the breast, ovary, or colon.

3. The method of claim 1, further comprising administering one or more additional anti-cancer agents.

4. The method of claim 3, wherein the additional anti-cancer agent acts in a phase of the cell cycle other than the $G_2$-M phase.

5. The method of claim 1, further comprising administering radiation therapy.

6. A method of treating a cancer responsive to microtubule stabilization in a patient comprising administering to said patient in need of such treatment a therapeutically effective amount of a compound of formula:

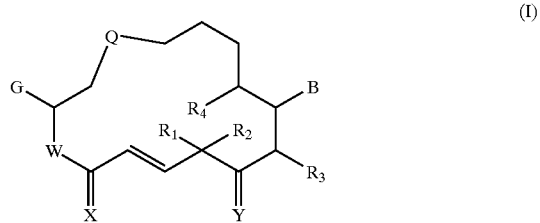

(I)

wherein:

Q is selected from the group consisting of:

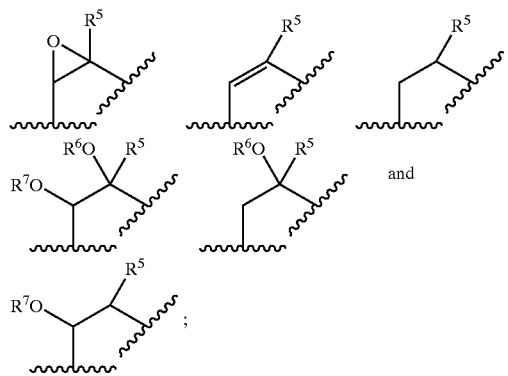

G is selected from the group consisting of: alkyl, substituted alkyl, aryl, substituted aryl, heterocyclo,

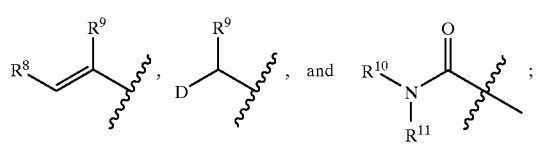

W is O;

X is O; S or H, H;

Y is selected from the group consisting of: O; $NOR_{15}$; $CHR_{19}$; H and H; H and $OR_{13}$; $OR_{14}$ and $OR_{14}$; H and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of: H, $OR_{20}$, $OCOR_{21}$, and $NR_{22}R_{23}$;

D is $NR_{25}R_{25}$ or saturated heterocyclo;

each $R_1$, $R_2$, $R_3$, and $R_4$ is, independently, H or lower alkyl;

each $R_{15}$ $R_{16}$, $R_{17}$, $R_{18}$, and $R_{19}$ is, independently, selected from the group consisting of: H alkyl, substituted alkyl, and aryl;

each $R_6$, $R_7$, $R_{13}$, $R_{14}$, $R_{20}$ and $R_{21}$ is, independently, selected from the group consisting of; H, alkyl and substituted alkyl;

each $R_5$, $R_9$, $R_{10}$, $R_{11}$, $R_{22}$, $R_{24}$, $R_{26}$ and $R_{27}$ is, independently, selected from the group consisting of: H, alkyl, substituted alkyl, aryl, heteroaryl, cycloalkyl and heterocyclo;

$R_8$ is selected from the group consisting of H, alkyl, substituted alkyl, cycloalkyl, and heterocyclo;

each $R_{23}$ and $R_{25}$ is, independently, selected from the group consisting of H, alkyl, substitute alkyl, aryl, heteroaryl, cycloalkyl, heterocyclo, $R_{26}C=O$, $R_{27}SO_2$, hydroxy, O-alkyl and O-substituted alkyl;

or pharmaceutically acceptable salts, hydrates, solvates, or stereoisomers thereof, with the proviso that compounds of the Formula (I) do not include compounds wherein each of:

X is O;

$R_1$, $R_2$, $R_3$, $R_4$ are methyl;

$R_5$ is H or methyl;

$R_5$ is H or methyl; and

G is 1-methyl-2-(2-methyl-4-thiazolyl)ethenyl.

7. A method of treating melanoma, non-Hodgkin's lymphoma, multiple myeloma, or Karposi's sarcoma in a patient in need of said treatment which comprises administering to said patient a therapeutically effective amount of a compound of formula:

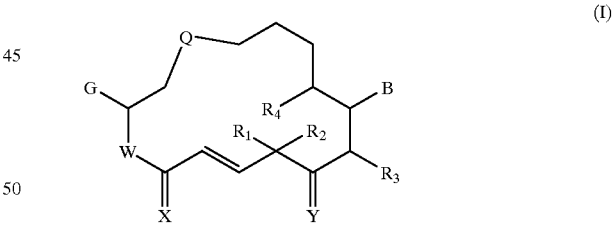

(I)

wherein:

Q is selected from the group consisting of:

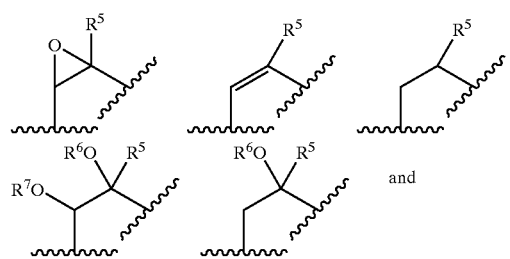

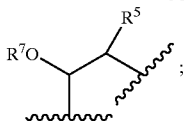

G is selected from the group consisting of: alkyl, substituted alkyl, aryl, substituted aryl, heterocyclo,

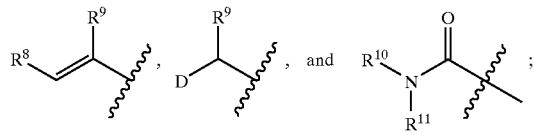

W is O;

X is O; S; or H, H;

Y is selected from the group consisting of: O; $NOR_{15}$; $CHR_{19}$; H and H; H and $OR_{13}$; $OR_{14}$ and $OR_{14}$; H and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of: H, $OR_{20}$, $OCOR_{21}$, and $NR_{22}R_{23}$;

D is $NR_{24}R_{25}$ or saturated heterocyclo;

each $R_1$, $R_2$, $R_3$, and $R_4$ is, independently, H or lower alkyl;

each $R_{15}$, $R_{16}$, $R_{17}$, $R_{18}$, and $R_{19}$ is, independently, selected from the group consisting of: H, alkyl, substituted alkyl, and aryl;

each $R_6$, $R_7$, $R_{13}$, $R_{14}$, $R_{20}$ and $R_{21}$ is, independently, selected from the group consisting of: H, alkyl and substituted alkyl;

each $R_5$, $R_9$, $R_{10}$, $R_{11}$, $R_{22}$, $R_{24}$, $R_{26}$ and $R_{27}$ is, independently, selected from the group consisting of: H, alkyl, substituted alkyl, aryl, heteroaryl, cycloalkyl and heterocyclo;

$R_8$ is selected from the group consisting of H, alkyl, substituted alkyl, cycloalkyl and heterocyclo;

each $R_{23}$ and $R_{25}$ is, independently, selected from the group consisting of: H, alkyl, substitute alkyl, aryl, heteroaryl, cycloalkyl, heterocyclo, $R_{26}C=O$, $R_{27}SO_2$, hydroxy, O-alkyl and O-substituted alkyl;

or pharmaceutically acceptable salts, hydrates, solvates, or stereoisomers thereof, with the proviso that compounds of the Formula I do not include compounds wherein each of:

X is O;

$R_1$, $R_{2, R3}$, $R_4$ are methyl;

$R_5$ is H or methyl;

$R_5$ is H or methyl; and

G is 1-methyl-2-(2-methyl-4-thiazolyl)ethenyl.

8. A method of treating breast cancer, ovarian cancer, colon cancer, head and neck cancer, lung cancer, cervical cancer, uterine cancer, brain cancer, germ cell cancer, urothelial cancer, esophageal cancer, prostrate cancer, bladder cancer or pancreatic cancer in a patient in need of said treatment which comprises administering to said patient a therapeutically effective amount of a compound of formula:

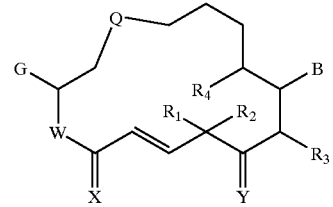

(I)

wherein:

Q is selected from the group consisting of:

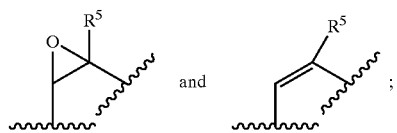

G is selected from the group consisting of: alkyl, substituted alkyl, aryl, substituted aryl,

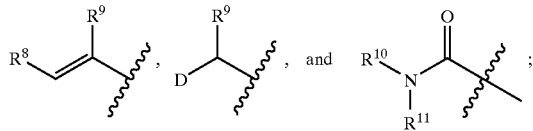

heterocyclo,

W is O;

X is O; S; or H, H;

Y is O;

B is selected from the group consisting of: H, $OR_{20}$, $OCOR_{21}$, and $NR_{22}R_{23}$;

D is $NR_{24}R_{25}$ or saturated heterocyclo;

each $R_1$, $R_2$, $R_3$, and $R_4$ is, independently, H or lower alkyl;

each $R_{20}$ a d $R_{21}$ is, independently, selected from the group consisting of: H, alkyl and substituted alkyl;

each $R_5$, $R_9$, $R_{10}$, $R_{11}$, $R_{22}$, $R_{24}$, $R_{26}$ and $R_{27}$ is, independently, selected from the group consisting f: H, alkyl, substituted alkyl, aryl, heteroaryl, cycloalkyl and heterocyclo;

$R_8$ is selected from the group consisting of: H, alkyl, substituted alkyl, cycloalkyl and heterocyclo;

each $R_{23}$ and $R_{25}$ is, independently, selected from the group consisting of: H, alkyl, substituted alkyl, aryl, heteroaryl, cycloalkyl, heterocyclo, $R_{26}C=O$, $R_{27}SO_2$, hydroxy, O-alkyl and O-substitute alkyl;

or pharmaceutically acceptable salts, hydrates, solvates, or stereoisomers thereof, with the proviso that compounds of the Formula (I) do not include compounds wherein each of:

X is O;

$R_1$, $R_2$, $R_3$, $R_4$ are methyl;

$R_5$ is H or methyl; and

G is 1-methyl-2-(2-methyl-4-thiazolyl)ethenyl.

9. The method of claim 8, wherein the cancer is cancer of the breast, ovary, or colon.

10. The method of claim 8, further comprising administering one or more additional anti-cancer agents.

11. The method of claim 10, wherein the additional anti-cancer agent acts in a phase of the cell cycle other than the $G_2$-M phase.

12. The method of claim 8, further comprising administering radiation therapy.

13. A method of treating a cancer responsive to microtubule stabilization in a patient comprising administering to said patient in need of such treatment a therapeutically effective amount of a compound of formula:

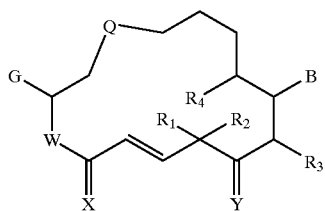

Q is selected from the group consisting of

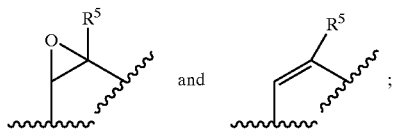

G is selected from the group consisting of: alkyl, aryl, substituted aryl, heterocyclo,

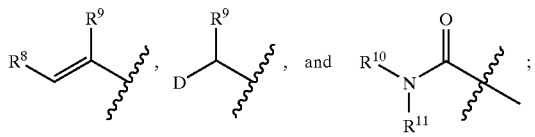

W is O;

X is O; S; or H, H;

Y is O;

B is selected from the group consisting of: H, $OR_{20}$, $OCOR_{21}$, and $NR_{22}R_{23}$;

D is $NR_{24}R_{25}$ or saturated heterocyclo;

each $R_1$, $R_2$, $R_3$, and $R_4$ is, independently, H or lower alkyl;

each $R_{20}$ and $R_{21}$ is, independently, selected from the group consisting of: H, alkyl and substituted alkyl;

each $R_5$, $R_9$, $R_{10}$, $R_{11}$, $R_{22}$, $R_{24}$, $R_{26}$ and $R_{27}$ is, independently, selected from the group consisting of: H, alkyl, substituted alkyl, aryl, heteroaryl, cycloalkyl and heterocyclo;

$R_8$ is selected from the group consisting of: H, alkyl, substituted alkyl, cycloalkyl, and heterocyclo;

each $R_{23}$ nd $R_{25}$ is, independently, selected from the group consisting of: H, alkyl, substituted alkyl, aryl, heteroaryl, cycloalkyl, heterocyclo, $R_{26}C=O$, $R_{27}SO_2$, hydroxy, O-alkyl and O-substitute alkyl;

or pharmaceutically acceptable salts, hydrates, solvates, or stereoisomers thereof, with the proviso that compounds of the Formula (I) do not include compounds wherein each of:

X is O;

$R_1$, $R_2$, $R_3$, $R_4$ are methyl;

$R_5$ is H or methyl; and

G is 1-methyl-2-(2-methyl-4-thiazolyl)ethenyl.

14. A method of treating melanoma, non-Hodgkin's lymphoma, multiple myeloma, or Karposi's sarcoma in a patient in need of said treatment which comprises administering to said patient a therapeutically effective amount of a compound of formula.

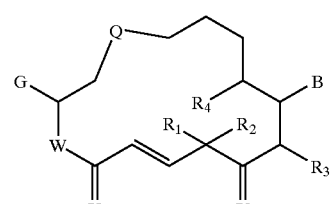

wherein:

Q is selected from the group consisting of:

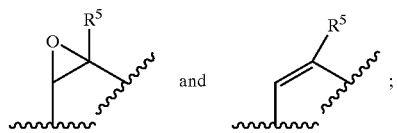

G is selected from the group consisting of: alkyl, aryl, substituted aryl, heterocyclo,

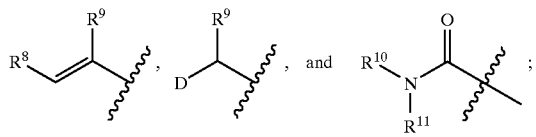

W is O;

X is O; S; or H, H;

Y is O;

B is select d from the group consisting of: H, $OR_{20}$, $OCOR_{21}$, and $NR_{22}R_{23}$;

D is $NR_{24}R_{25}$ or saturated heterocyclo;

each $R_1$, $R_2$, $R_3$, and $R_4$ is, independently, H or lower alkyl;

each $R_{20}$ and $R_{21}$ is, independently, selected from the group consisting of: H, alkyl and substituted alkyl;

each $R_5$, $R_9$, $R_{10}$, $R_{11}$, $R_{22}$, $R_{24}$, $R_{26}$ and $R_{27}$ is, independently, selected from the group consisting of: H, alkyl, substituted alkyl, aryl, heteroaryl, cycloalkyl and heterocyclo;

$R_8$ is selected from the group consisting of: H, alkyl, substituted alkyl, cycloalkyl, and heterocyclo;

each $R_{23}$ and $R_{25}$ is, independently, selected from the group consisting of: H, alkyl, substituted alkyl, aryl, heteroaryl, cycloalkyl, heterocyclo, $R_{26}C=O$, $R_{27}SO_2$, hydroxy, O-alkyl and O-substitute alkyl;

or pharmaceutically acceptable salts, hydrates, solvates, or stereoisomers thereof, with the proviso that compounds of the Formula (I) do not include compounds wherein each of:

X is O;

$R_1$, $R_2$, $R_3$, $R_4$ are methyl;

$R_5$ is H or ethyl;

G is 1-methyl-2-(2-methyl-4-thiazolyl)ethenyl.

15. A method of treating breast cancer, ovary cancer, colon cancer, head and neck cancer, lung cancer, cervical cancer, uterine cancer, brain cancer, germ cell cancer, urothelial cancer, esophageal cancer, prostrate cancer, bladder cancer, or pancreatic cancer in a patient in need of said treatment which comprises administering to said patient a therapeutically effective amount of a compound of the formula:

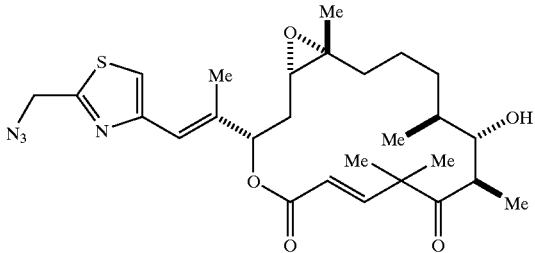

or a pharmaceutically acceptable salt, hydrate, solvate, or stereoisomer thereof.

16. The method of claim 15, wherein the cancer is cancer of the breast, ovary, or colon.

17. The method of claim 15, further comprising administering one or more additional anti-cancer agents.

18. The method of claim 17, wherein the additional anti-cancer agent acts in a phase of the cell cycle other than the $G_2$-M phase.

19. The method of claim 15, further comprising administering radiation therapy.

20. A method of treating a cancer responsive to microtubule stabilization in a patient comprising administering to a said patient in need of such treatment a therapeutically effective amount of a compound of the formula:

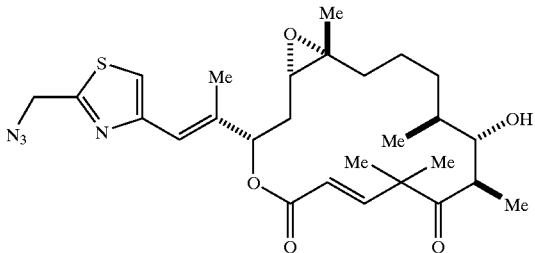

or a pharmaceutically acceptable salt, hydrate, solvate, or stereoisomer thereof.

21. A method of treating melanoma, non-Hodgkin's lymphoma, multiple myeloma, or Karposi's sarcoma in a patient in need of said treatment which comprises administering to said patient a therapeutically effective amount of a compound of the formula:

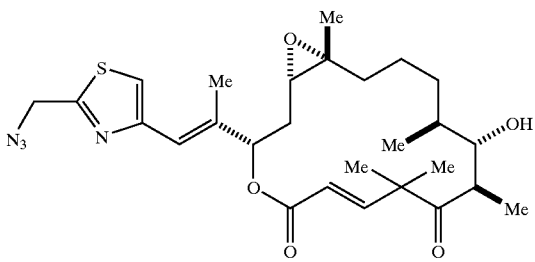

or a pharmaceutically acceptable salt, hydrate, solvate, or stereoisomer thereof.

22. A method of treating breast cancer, ovarian cancer, colon cancer, head and neck cancer, lung cancer, cervical cancer, uterine cancer, brain cancer, germ cell cancer, urothelial cancer, esophageal cancer, prostrate cancer, bladder cancer, or pancreatic cancer in a patient in need of said treatment which comprises administering to said patient a therapeutically effective amount of the compound of the formula:

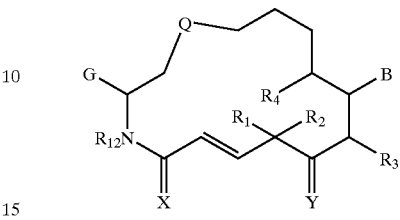

wherein:

Q is selected from the group consisting of:

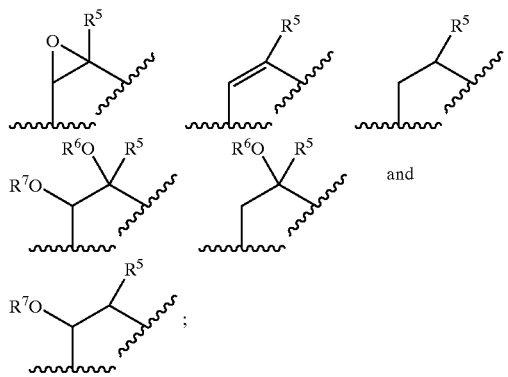

G is selected from the group consisting of: alkyl, substituted alkyl, aryl, substituted

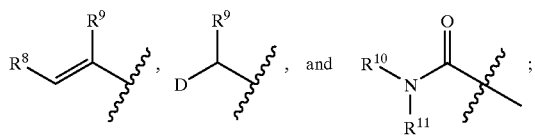

aryl, heterocyclo,

X is O; S; or H, H;

Y is selected from the group consisting of: O; $NOR_{15}$; $CHR_{19}$; H and H; H and $OR_{13}$; $OR_{14}$ and $OR_{14}$; and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of: H, $OR_{20}$, $OCOR_{21}$, and $NR_{22}R_{23}$;

D is $NR_{24}R_5$ or saturated heterocyclo;

each $R_1$, $R_2$, $R_3$, and $R_4$ is, independently, H or lower alkyl;

each $R_{15}$, $R_{16}$, $R_{17}$, $R_{18}$, and $R_{19}$ is, independently, selected from the group consisting of: H, alkyl, substituted alkyl and aryl;

each $R_6$, $R_7$, $R_{13}$, $R_{14}$, $R_{20}$ and $R_{21}$ is, independently, selected from the group consisting of: H, alkyl and substituted alkyl;

each $R_5$, $R_8$, $R_9$, $R_{10}$, $R_{11}$, $R_{22}$, $R_{24}$, $R_{26}$ and $R_{27}$ is, independently, selected from the group consisting of: H, alkyl, substituted alkyl, aryl, heteroaryl, cycloalkyl and heterocyclo;

each $R_{12}$, $R_{23}$, and $R_{25}$ is, independently, selected from the group consisting of: H, alkyl, substituted alkyl, aryl, heteroaryl, cycloalkyl, heterocyclo, $R_{26}C=O$, $R_{27}SO_2$, hydroxy, O-alkyl and O-substituted alkyl;

or pharmaceutically acceptable salts, hydrates, solvates, or stereoisomers thereof.

23. The method of claim 22, wherein the cancer is cancer of the breast, ovary or colon.

24. The method of claim 22, further comprising administering one or more additional anti-cancer agents.

25. The method of claim 24, wherein the additional anti-cancer agent acts in a phase of the cell cycle other than the $G_2$-M phase.

26. The method of claim 22, further comprising administering radiation therapy.

27. A method of treating a cancer responsive to microtubule stabilization in a patient comprising administering to a said patient in need of such treatment a therapeutically effective amount of a compound of the formula:

wherein:

Q is selected from the group consisting of:

G is selected from the group consisting of: alkyl, substituted alkyl, aryl, substituted aryl, heterocyclo, X is O; S; or H, H;

Y is selected from the group consisting of: O; $NOR_{15}$; $CHR_{19}$; H and H; H and $OR_{13}$; $OR_{14}$ and $OR_{14}$; and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of: H, $OR_{20}$, $OCOR_{21}$, and $NR_{22}R_{23}$;

D is $NR_{24}R_{25}$ or saturated heterocyclo;

each $R_1$, $R_2$, $R_3$, and $R_4$ is, independently, H or lower alkyl;

each $R_{15}$, $R_{16}$, $R_{17}$, $R_{18}$, and $R_{19}$ is, independently, selected from the group consisting of: H, alkyl, substituted alkyl and aryl;

each $R_6$, $R_7$, $R_{13}$, $R_{14}$, $R_{20}$ and $R_{21}$ is, independently, selected from the group consisting of: H, alkyl and substituted alkyl;

each $R_5$, $R_8$, $R_9$, $R_{10}$, $R_{11}$, $R_{22}$, $R_{24}$, $R_{26}$ and $R_{27}$ is, independently, selected from the group consisting of: H, alkyl, substituted alkyl, aryl, heteroaryl, cycloalkyl and heterocyclo;

each $R_{12}$, $R_{23}$, and $R_{25}$ is, independently, selected from the group consisting of: H, alkyl, substituted alkyl, aryl, heteroaryl, cycloalkyl, heterocyclo, $R_{26}C=O$, $R_{27}SO_2$, hydroxy, O-alkyl and O-substituted alkyl;

or pharmaceutically acceptable salts, hydrates, solvates, or stereoisomers thereof.

28. A method of treating melanoma, non-Hodgkin's lymphoma, multiple myeloma, or Karposi's sarcoma in a patient in need of said treatment which comprises administering to said patient a therapeutically effective amount of a compound of the formula:

wherein:

Q is selected from the group consisting of:

G is selected from the group consisting of: alkyl, substituted alkyl, aryl, substituted aryl, heterocyclo, X is O; S; or H, H;

Y is selected from the group consisting of: O; $NOR_{15}$; $CHR_{19}$; H and H; H and $OR_{13}$; $OR_{14}$ and $OR_{14}$; and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of: H, $OR_{20}$, $OCOR_{21}$, and $NR_{22}R_{23}$;

D is $NR_{24}R_{25}$ or saturated heterocyclo;

each $R_1$, $R_2$, $R_3$, and $R_4$ is, independently, H or lower alkyl;

each $R_{15}$, $R_{16}$, $R_{17}$, $R_{18}$, and $R_{19}$ is, independently, selected from the group consisting of: H, alkyl, substituted alkyl and aryl;

each $R_6$, $R_7$, $R_{13}$, $R_{14}$, $R_{20}$ and $R_{21}$ is, independently, selected from the group consisting of: H, alkyl and substituted alkyl;

each $R_5$, $R_8$, $R_9$, $R_{10}$, $R_{11}$, $R_{22}$, $R_{24}$, $R_{26}$ and $R_{27}$ is, independently, selected from the group consisting of: H, alkyl, substituted alkyl, aryl, heteroaryl, cycloalkyl and heterocyclo;

each $R_{12}$, $R_{23}$, and $R_{25}$ is, independently, selected from the group consisting of: H, alkyl, substituted alkyl, aryl, heteroaryl, cycloalkyl, heterocyclo, $R_{26}C=O$, $R_{27}SO_2$, hydroxy, O-alkyl and O-substituted alkyl;

or pharmaceutically acceptable salts, hydrates, solvates, or stereoisomers thereof.

29. A method of treating breast cancer, ovarian cancer, colon cancer, head and neck cancer, lung cancer, cervical cancer, uterine cancer, brain cancer, germ cell cancer, urothelial cancer, esophageal cancer, prostrate cancer, bladder cancer, or pancreatic cancer in a patient in need of said treatment which comprises administering to said patient a therapeutically effective amount of the compound of the formula:

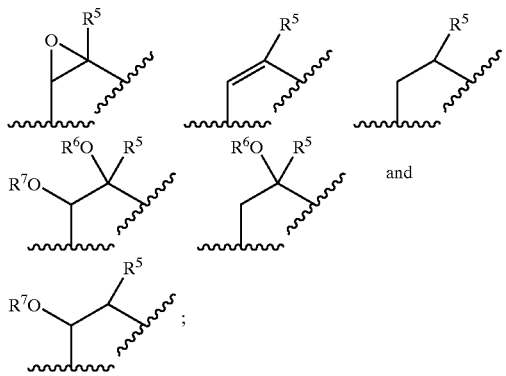

wherein:

Q is selected from the group consisting of:

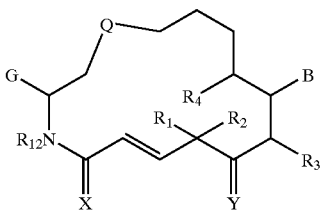

G is selected from the group consisting of: alkyl; substituted alkyl, wherein said substituent is selected from halogen, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines, alkanoylamino, aroylamino, aralkanoylamino, thiol, alkylthio, arylthio, cycloalkylthio, heterocyclothio, alkylthiono, arylthiono, alkylsulfonyl, arylsulfonyl, aralkylsulfonyl, sulfonamido, substituted sulfonamido, nitro, cyano, carboxy, carbamyl, substituted carbamyl, alkoxycarbonyl, aryl, substituted aryl, guanadino and heterocyclo; aryl, optionally substituted with one to four substituents selected from alkyl, substituted alkyl, phenyl, halogen, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, and aryloxy; a heterocyclo,

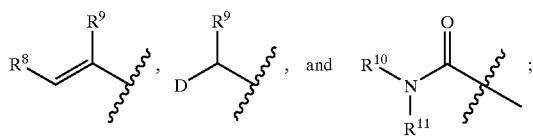

wherein heterocyclo includes optionally substituted 4 to 7 membered monocyclic, 7 to 11 membered bicyclic, or 10 to 15 membered tricyclic ring systems with between 1 and 3 heteroatoms selected from nitrogen, oxygen, and sulfur atoms in at least one carbon atom-containing ring;

X is O; S; or H, H;

Y is selected from the group consisting of O; $NOR_{15}$; $CHR_{19}$; H and H; H and $OR_{13}$; $OR_{14}$ and $OR_{14}$; H and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of H, $OR_{20}$, $OCOR_{21}$, and $NR_{22}R_{23}$;

D is $NR_{24}R_{25}$ or saturated heterocycle;

each $R_1$, $R_2$, $R_3$, and $R_4$ is, independently, H or lower alkyl;

each $R_{15}$, $R_{16}$, $R_{17}$, $R_{18}$, and $R_{19}$ is, independently, selected from the group consisting of H, alkyl, substituted alkyl and aryl;

each $R_6$, $R_7$, $R_{13}$, $R_{14}$, $R_{20}$ and $R_{21}$ is, independently, selected from the group consisting of H, alkyl and substituted alkyl;

each $R_5$, $R_8$, $R_9$, $R_{10}$, $R_{11}$, $R_{22}$, $R_{24}$, $R_{26}$ and $R_{27}$ is, independently, selected from the group consisting of H, alkyl, substituted alkyl, aryl, heteroaryl, cycloalkyl and heterocyclo;

each $R_{12}$, $R_{23}$ $R_{25}$ is, independently, selected from the group consisting of H, alkyl, substituted alkyl, aryl, heteroaryl, cycloalkyl, heterocyclo, $R_{26}C=O$, $R_{27}SO_2$, hydroxy, O-alkyl and O-substituted alkyl;

or harmaceutically acceptable salts, hydrates, solvates, or stereoisomers thereof.

30. The method of claim 29, wherein the cancer is cancer of the breast, ovary or colon.

31. The method of claim 29, further comprising administering one or more additional anti-cancer agents.

32. The method of claim 31, wherein the additional anti-cancer agent acts in a phase of the cell cycle other than the $G_2$-M phase.

33. The method of claim 29, further comprising administering radiation therapy.

34. A method of treating a cancer responsive to microtubule stabilization in a patient comprising administering to said patient in need of such treatment a therapeutically effective amount of a compound of the formula:

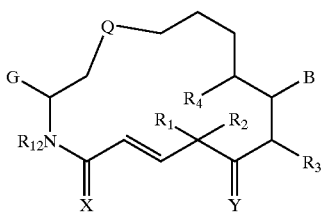

wherein:

Q is selected from the group consisting of:

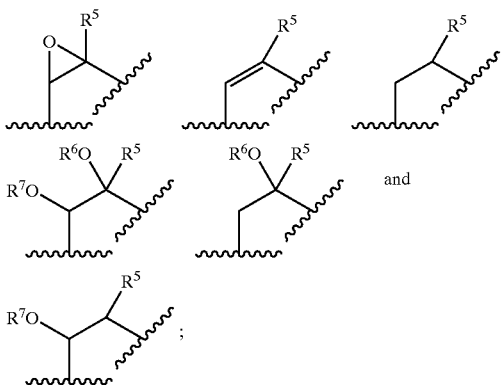

G is selected from the group consisting of: alkyl; substituted alkyl, wherein said substituent is selected from halogen, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines, alkanoylamino, aroylamino, aralkanoylamino, thiol, alkylthio, arylthio, cycloalkylthio, heterocyclothio, alkylthiono, arylthiono, alkylsulfonyl, arylsulfonyl, aralkylsulfonyl, sulfonamido, substituted sulfonamido, nitro, cyano, carboxy, carbamyl, substituted carbamyl, alkoxycarbonyl, aryl, substituted aryl, guanadino and heterocyclo; aryl, optionally substituted with one to four substituents selected from alkyl, substituted alkyl, phenyl, halogen, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, and aryloxy; a heterocyclo,

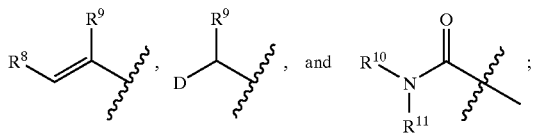

wherein heterocyclo includes optionally substituted 4 to 7 membered monocyclic, 7 to 11 membered bicyclic, or 10 to 15 membered tricyclic ring systems with between 1 and 3 heteroatoms selected from nitrogen, oxygen, and sulfur atoms in at least one carbon atom-containing ring;

X is O; S; or H, H;

Y is selected from the group consisting of O; $NOR_{15}$; $CHR_{19}$; H and H; H and $OR_{13}$; $OR_{14}$ and $OR_{14}$; and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of H, $OR_{20}$, $OCOR_{21}$, and $NR_{22}R_{23}$;

D is $NR_{24}R_{25}$ saturated heterocycle;

each $R_1$, $R_2$, $R_3$, and $R_4$ is, independently, H or lower alkyl;

each $R_{15}$, $R_{16}$, $R_{17}$, $R_{18}$, and $R_{19}$ is, independently, selected from the group consisting of H, alkyl, substituted alkyl and aryl;

each $R_6$, $R_7$, $R_{13}$, $R_{14}$, $R_{20}$ and $R_{21}$ is, independently, selected from the group consisting of H, alkyl and substituted alkyl;

each $R_5$, $R_8$, $R_9$, $R_{10}$, $R_{11}$, $R_{22}$, $R_{24}$, $R_{26}$ and $R_{27}$ is, independently, selected from the group consisting of H, alkyl, substituted alkyl, aryl, heteroaryl, cycloalkyl and heterocyclo;

each $R_{12}$, $R_{23}$ and $R_{25}$ is, independently, selected from the group consisting of H, alkyl, substituted alkyl, aryl, heteroaryl, cycloalkyl, heterocyclo, $R_{26}C=O$, $R_{27}SO_2$, hydroxy, O-alkyl and O-substituted alkyl;

or pharmaceutically acceptable salts, hydrates, solvates, or stereoisomers thereof.

35. A method of treating a cancer responsive to microtubule stabilization in a patient comprising administering to said patient in need of such treatment a therapeutically effective amount of a compound of the formula:

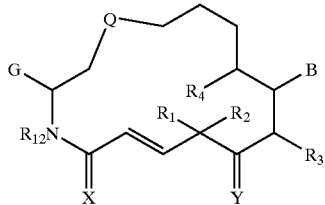

wherein:

Q is selected from the group consisting of:

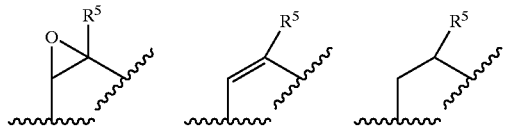

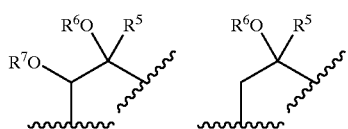

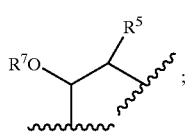

G is selected from the group consisting of: alkyl, substituted alkyl, aryl, substituted

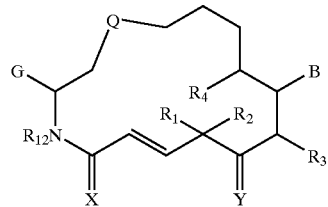

aryl, heterocyclo,

X is O; S; or H, H;

Y is selected from the group consisting of: O; $NOR_{15}$; $CHR_{19}$; H and H; H and $OR_{13}$; $OR_{14}$ and $OR_{14}$; and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of: H, $OR_{20}$, $OCOR_{21}$, and $NR_{22}R_{23}$;

D is $NR_{24}R_{25}$ saturated heterocyclo;

each $R_1$, $R_2$, $R_3$, and $R_4$ is, independently, H or lower alkyl;

each $R_{15}$, $R_{16}$, $R_{17}$, $R_{18}$, and $R_{19}$ is, independently, selected from the group consisting of: H, alkyl, substituted alkyl and aryl;

each $R_6$, $R_7$, $R_{13}$, $R_{14}$, $R_{20}$ and $R_{21}$ is, independently, selected from the group consisting of: H, alkyl and substituted alkyl;

each $R_5$, $R_8$, $R_9$, $R_{10}$, $R_{11}$, $R_{22}$, $R_{24}$, $R_{26}$ and $R_{27}$ is, independently, selected from the group consisting of: H, alkyl, substituted alkyl, aryl, heteroaryl, cycloalkyl and heterocyclo;

each $R_{12}$, $R_{23}$, and $R_{25}$ is, independently, selected from the group consisting of: H, alkyl, substituted alkyl, aryl, heteroaryl, cycloalkyl, heterocyclo, $R_{26}C=O$, $R_{27}SO_2$, hydroxy, O-alkyl and O-substituted alkyl;

or pharmaceutically acceptable salts, hydrates, solvates, or stereoisomers thereof.

36. A method of treating melanoma, non-Hodgkin's lymphoma, multiple myeloma, or Karposi's sarcoma in a patient in need of said treatment which comprises administering to said patient a therapeutically effective amount of a compound of the formula:

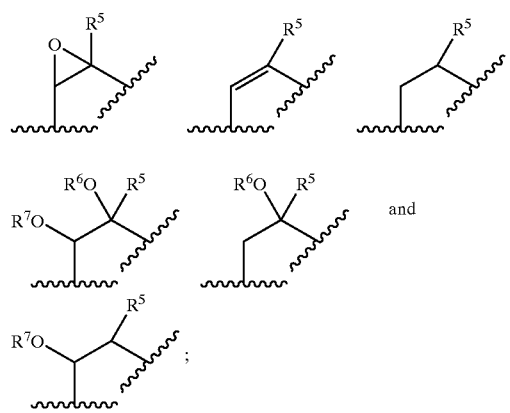

wherein:

Q is selected from the group consisting of:

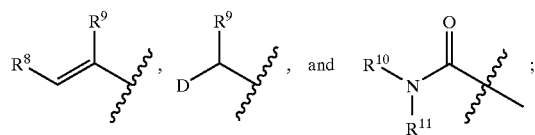

G is select from the group consisting of: alkyl; substituted alkyl, wherein said substituent is selected from halogen, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines, alkanoylamino, aroylamino, aralkanoylamino, thiol, alkylthio, arylthio, cycloalkylthio, heterocyclothio, alkylthiono, arylthiono, alkylsulfonyl, arylsulfonyl, aralkylsulfonyl, sulfonamido, substituted sulfonamido, nitro, cyano, carboxy, carbamyl, substituted carbamyl, alkoxycarbonyl, aryl, substituted aryl, guanadino and heterocyclo; aryl, optionally substituted with one to four substituents selected from alkyl, substituted alkyl, phenyl, halogen, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, and aryloxy; a heterocyclo,

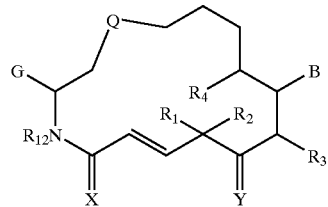

wherein heterocyclo includes optionally substituted 4 to 7 membered monocyclic, 7 to 11 membered bicyclic, or 10 to 15 membered tricyclic ring systems with between 1 and 3 heteroatoms selected from nitrogen, oxygen, and sulfur atoms in at least one carbon atom-containing ring;

X is O; S; or H, H;

Y is selected from the group consisting of O; $NOR_{15}$; $CHR_{19}$; H and H; H and $OR_{13}$; $OR_{14}$ and $OR_{14}$; and $NR_{17}R_{18}$; and H and $NHOR_{16}$, wherein when Y is $OR_{14}$, $OR_{14}$ the $R_{14}$ groups can be joined to form a cyclic ketal;

B is selected from the group consisting of H, $OR_{20}$, $OCOR_{21}$, and $NR_{22}R_{23}$;

D is $NR_{24}R_{25}$ saturated heterocycle;

each $R_1$, $R_2$, $R_3$, and $R_4$ is, independently, H or lower alkyl;

each $R_{15}$, $R_{16}$, $R_{17}$, $R_{18}$, and $R_{19}$ is, independently, selected from the group consisting of H, alkyl, substituted alkyl and aryl;

each $R_6$, $R_7$, $R_{13}$, $R_{14}$, $R_{20}$ and $R_{21}$ is, independently, selected from the group consisting of H, alkyl and substituted alkyl;

each $R_5$, $R_8$, $R_9$, $R_{10}$, $R_{11}$, $R_{22}$, $R_{24}$, $R_{26}$ and $R_{27}$ is, independently, selected from the group consisting of H, alkyl, substituted alkyl, aryl, heteroaryl, cycloalkyl and heterocyclo;

each $R_{12}$, $R_{23}$ $R_{25}$ is, independently, selected from the group consisting of H, alkyl, substituted alkyl, aryl, heteroaryl, cycloalkyl, heterocyclo, $R_{26}C=O$, $R_{27}SO_2$, hydroxy, O-alkyl and O-substituted alkyl;

or pharmaceutically acceptable salts, hydrates, solvates, or stereoisomers thereof.

* * * * *

UNITED STATES PATENT AND TRADEMARK OFFICE
CERTIFICATE OF CORRECTION

PATENT NO. : 6,831,090 B2
APPLICATION NO. : 10/242437
DATED : December 14, 2004
INVENTOR(S) : Vite et al.

It is certified that error appears in the above-identified patent and that said Letters Patent is hereby corrected as shown below:

Column 19, line 62, "head a d neck cancer" should read:  --head and neck cancer--

Column 19, line 63, "rain cancer," should read:  --brain cancer--

Column 19, line 63, Column 23, line 64, Column 27, line 1, Column 28, line 2, and Column 31, line 29, "prostrate cancer," each occurrence, should read: --prostate cancer--

Column 20, lines 42-46, "OR14 an OR14;" should read:  --OR14 and OR14;--

Column 20, lines 53-57, "each R15, R16, R17, R18, and R19 is, independently, selected from the group consisting of: H alkyl, substituted alkyl, and aryl; each R6, R7, R13, R14, R20 and R21 is, independently, selected from the group consisting of: H alkyl and substituted alkyl;" should read:
   --each R15, R16, R17, R18, and R19 is, independently, selected from the group consisting of: H, alkyl, substituted alkyl, and aryl;
      each R6, R7, R13, R14, R20 and R21 is, independently, selected from the group consisting of: H, alkyl, and substituted alkyl;--

Column 20, lines 65-67, "substitute alkyl, aryl, heteroaryl, cycloalkyl, heterocyclo, R26C=O, R27SO2, hydroxy, O-alky and O-substituted alkyl;" should read:
  --substituted alkyl, aryl, heteroaryl, cycloalkyl, heterocyclo, R26C=O, R27SO2, hydroxy, O-alkyl and O-substituted alkyl;--

Column 22, line 22, and Column 23, line 47, "substitute alkyl," each occurrence, should read: --substituted alkyl--

Column 22, line 34, and Column 23, line 57, each occurrence, cancel the text "R5 is H or methyl;"

Column 23, line 56, "$R_1$, $R_2$, $R_3$, $R_4$ are methyl;" should read: --$R_1$, $R_2$, $R_3$, $R_4$ are methyl;--

UNITED STATES PATENT AND TRADEMARK OFFICE
CERTIFICATE OF CORRECTION

PATENT NO.       : 6,831,090 B2
APPLICATION NO.  : 10/242437
DATED            : December 14, 2004
INVENTOR(S)      : Vite et al.

It is certified that error appears in the above-identified patent and that said Letters Patent is hereby corrected as shown below:

Column 24, lines 21-31, "G is selected from the group consisting of: alkyl, substituted alkyl, aryl, substituted aryl,

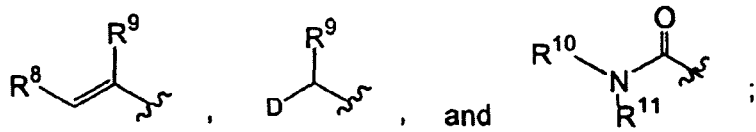

heterocyclo," should read:
--G is selected from the group consisting of: alkyl, substituted alkyl, aryl, substituted aryl, heterocyclo,

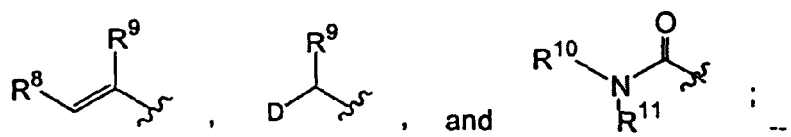

Column 24, line 40, "each $R_{20}$ a d $R_{21}$ is," should read: --each $R_{20}$ and $R_{21}$ is,--.

Column 24, line 43, "selected from the group consisting f:" should read: --selected from the group consisting of:--

Column 24, line 51 and Column 26, line 55, "O-substitute alkyl;" each occurrence, should read: --O-substituted alkyl;--

Column 25, line 53, "each $R_{23}$ nd $R_{25}$ is," should read: --each $R_{23}$ and $R_{25}$ is--

Column 26, line 38, "B is select d from the group consisting of:" should read:
--B is selected from the group consisting of:--

Column 26, line 63, "$R_5$ is H or ethyl;" should read: --$R_5$ is H or methyl;--

UNITED STATES PATENT AND TRADEMARK OFFICE
CERTIFICATE OF CORRECTION

PATENT NO.       : 6,831,090 B2
APPLICATION NO.  : 10/242437
DATED            : December 14, 2004
INVENTOR(S)      : Vite et al.

It is certified that error appears in the above-identified patent and that said Letters Patent is hereby corrected as shown below:

Column 28, lines 36-45, Column 29, lines 49-59, Column 30, lines 54-64, and Column 35, lines 15-29, "G is selected from the group consisting of: alkyl, substituted alkyl, aryl, substituted

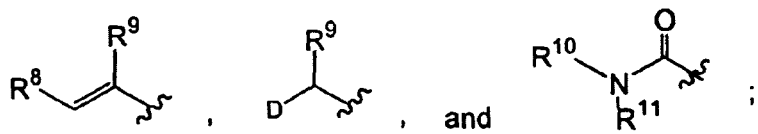

aryl, heterocyclo," each occurrence, should read:
--G is selected from the group consisting of: alkyl, substituted alkyl, aryl, substituted aryl, heterocyclo,

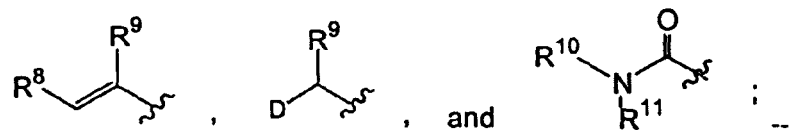

Column 28, lines 48-49, Column 29, lines 62-63, Column 30, line 67 to Column 31, line 1, Column 34, lines 17-18, Column 35, lines 32-33, and Column 37, lines 6-7, "$OR_{14}$ and $OR_{14}$; and $NR_{17}R_{18}$;" each occurrence, should read:   --$OR_{14}$ and $OR_{14}$; and H and $NR_{17}R_{18}$;--

Column 28, line 54, "D is $NR_{24}R_5$ or saturated heterocyclo;" should read:
--D is $NR_{24}R_{25}$ or saturated heterocyclo;--

Column 32, line 59, "harmaceutically acceptable salts," should read:
--pharmaceutically acceptable salts,--

UNITED STATES PATENT AND TRADEMARK OFFICE
CERTIFICATE OF CORRECTION

PATENT NO. : 6,831,090 B2
APPLICATION NO. : 10/242437
DATED : December 14, 2004
INVENTOR(S) : Vite et al.

It is certified that error appears in the above-identified patent and that said Letters Patent is hereby corrected as shown below:

Column 34, line 24, Column 35, line 39, and Column 37, line 13, "D is $NR_{24}R_{25}$ saturated heterocycle;" each occurrence, should read:    --D is $NR_{24}R_{25}$ or saturated heterocycle;--

Signed and Sealed this

Seventeenth Day of October, 2006

JON W. DUDAS
*Director of the United States Patent and Trademark Office*